US012678481B2

(12) United States Patent
Bauzon et al.

(10) Patent No.: US 12,678,481 B2
(45) Date of Patent: ***Jul. 14, 2026

(54) GLA DOMAINS AS THERAPEUTIC AGENTS

(71) Applicant: GLADIATOR BIOSCIENCES, INC., Mill Valley, CA (US)

(72) Inventors: Maxine Bauzon, Hercules, CA (US); Terry Hermiston, Mill Valley, CA (US)

(73) Assignee: GLADIATOR BIOSCIENCES, INC., Mill Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,162

(22) Filed: Sep. 25, 2020

(65) Prior Publication Data

US 2021/0015900 A1    Jan. 21, 2021

Related U.S. Application Data

(63) Continuation of application No. 16/170,131, filed on Oct. 25, 2018, now Pat. No. 10,925,926, which is a continuation of application No. 15/631,937, filed on Jun. 23, 2017, now abandoned, which is a continuation of application No. 14/773,068, filed as application No. PCT/US2014/026237 on Mar. 13, 2014, now Pat. No. 9,694,048.

(60) Provisional application No. 61/791,537, filed on Mar. 15, 2013, provisional application No. 61/787,753, filed on Mar. 15, 2013.

(51) Int. Cl.
| | |
|---|---|
| *A61K 38/17* | (2006.01) |
| *A61K 38/16* | (2006.01) |
| *A61K 38/18* | (2006.01) |
| *A61K 45/06* | (2006.01) |
| *A61K 47/64* | (2017.01) |
| *A61N 5/10* | (2006.01) |
| *A61P 31/12* | (2006.01) |
| *C07K 14/485* | (2006.01) |
| *C07K 14/745* | (2006.01) |
| *C12N 9/64* | (2006.01) |
| *C12N 9/74* | (2006.01) |

(52) U.S. Cl.
CPC .......... *A61K 38/1709* (2013.01); *A61K 38/16* (2013.01); *A61K 38/1808* (2013.01); *A61K 45/06* (2013.01); *A61K 47/642* (2017.08); *A61N 5/10* (2013.01); *A61P 31/12* (2018.01); *C07K 14/485* (2013.01); *C07K 14/745* (2013.01); *C12N 9/6424* (2013.01); *C12N 9/6429* (2013.01); *C12N 9/6437* (2013.01); *C07K 2319/035* (2013.01); *C12Y 304/21005* (2013.01); *C12Y 304/21021* (2013.01); *Y02A 50/30* (2018.01)

(58) Field of Classification Search
CPC ................ A61K 38/16; A61K 38/1709; A61K 38/1808; A61K 45/06; A61K 47/642; A61N 5/10; C07K 14/485; C07K 14/745; C07K 2319/035; C12N 9/6424; C12N 9/6437
See application file for complete search history.

(56) References Cited

U.S. PATENT DOCUMENTS

| | | | |
|---|---|---|---|
| 5,440,013 A | 8/1995 | Kahn | |
| 5,446,128 A | 8/1995 | Kahn | |
| 5,475,085 A | 12/1995 | Kahn | |
| 5,597,457 A | 1/1997 | Craig et al. | |
| 5,618,914 A | 4/1997 | Kahn | |
| 5,656,484 A * | 8/1997 | Bouma ................ | C07K 14/745 |
| | | | 435/320.1 |
| 5,670,155 A | 9/1997 | Kahn | |
| 5,672,681 A | 9/1997 | Kahn | |
| 5,674,976 A | 10/1997 | Kahn | |
| 5,710,245 A | 1/1998 | Kahn | |
| 5,790,421 A | 8/1998 | Osslund | |
| 5,840,833 A | 11/1998 | Kahn | |
| 5,859,184 A | 1/1999 | Kahn et al. | |
| 5,889,155 A | 3/1999 | Ashkenazi et al. | |
| 5,929,237 A | 7/1999 | Kahn | |
| 6,093,573 A | 7/2000 | Beamer et al. | |
| 6,261,569 B1 | 7/2001 | Comis et al. | |
| 6,312,694 B1 | 11/2001 | Thorpe et al. | |
| 6,459,996 B1 | 10/2002 | Somers et al. | |
| 6,631,332 B2 | 10/2003 | Skolnick et al. | |
| 6,801,860 B1 | 10/2004 | Dessen et al. | |
| 7,511,016 B2 | 3/2009 | Reutelingsperger | |
| 8,283,167 B2 | 10/2012 | Simon | |
| 9,023,604 B2 | 5/2015 | Schmidt et al. | |
| 2003/0104578 A1 | 6/2003 | Balance | |

(Continued)

FOREIGN PATENT DOCUMENTS

| | | |
|---|---|---|
| AU | 2013/200991 | 4/2014 |
| CN | 101426906 | 6/2013 |

(Continued)

OTHER PUBLICATIONS

Renjing Wang, Structural Transitions of the RING1B C-Terminal Region upon Binding the Polycomb cbox Domain, Biochemistry. Aug. 5, 2008; 47(31): 8007-8015.*

(Continued)

*Primary Examiner* — Erinne R Dabkowski
(74) *Attorney, Agent, or Firm* — pH IP Law

(57) ABSTRACT

The disclosure relates to the recombinant Gla domain proteins and their use targeting phosphatidylserine (PtdS) moieties on the surface of cells, particularly those expressing elevated levels of PtdS, such as cells undergoing apoptosis.

10 Claims, 8 Drawing Sheets

Specification includes a Sequence Listing.

(56)                    References Cited

U.S. PATENT DOCUMENTS

| | | | |
|---|---|---|---|
| 2003/0220490 A1 | 11/2003 | Kuriyama et al. | |
| 2004/0001827 A1 | 1/2004 | Dennis | |
| 2005/0015232 A1 | 1/2005 | Reinherz et al. | |
| 2009/0098103 A1 | 4/2009 | Madison et al. | |
| 2009/0130060 A1 | 5/2009 | Weimer et al. | |
| 2009/0291890 A1* | 11/2009 | Madison ................ | C12N 15/62 |
| | | | 435/352 |
| 2010/0330059 A1* | 12/2010 | Stafford ......... | C12Y 304/21021 |
| | | | 435/320.1 |
| 2011/0159571 A1 | 6/2011 | Barry et al. | |
| 2016/0008482 A1 | 1/2016 | Bauzon et al. | |
| 2017/0224840 A1 | 8/2017 | Yao et al. | |

FOREIGN PATENT DOCUMENTS

| | | |
|---|---|---|
| CN | 105567642 | 5/2016 |
| CN | 106414503 | 2/2017 |
| EP | 2280024 | 2/2011 |
| JP | 2002-003407 | 1/2002 |
| JP | 2011-515075 | 5/2011 |
| RU | 2373282 | 11/2009 |
| WO | WO 2005/079766 | 9/2005 |
| WO | WO2006/031291 | 3/2006 |
| WO | WO 2006/079120 | 7/2006 |
| WO | WO 2010/006136 | 1/2010 |
| WO | WO 2010/037402 | 4/2010 |
| WO | WO 2010/151736 | 12/2010 |
| WO | WO 2011/094181 | 8/2011 |
| WO | WO 2012/087241 | 6/2012 |
| WO | WO 2012/120130 | 9/2012 |
| WO | WO2013/011011 | 1/2013 |
| WO | WO 2013/151665 | 10/2013 |
| WO | WO 2014/018535 | 1/2014 |
| WO | WO 2014/151535 | 3/2014 |
| WO | WO 2014/151683 | 9/2014 |
| WO | WO2015/138452 | 9/2015 |
| WO | WO 2017/118764 | 7/2017 |
| WO | WO 2019/050997 | 3/2019 |
| WO | WO 2019/050998 | 3/2019 |
| WO | WO 2019/051002 | 3/2019 |

OTHER PUBLICATIONS

Daniel M. Czajkowsky, Fc-fusion proteins: new developments and future perspectives, EMBO Mol Med (2012) 4, 1015-1028.*
Promega, An introduction to protein Expression, pp. 1-12, 2011.*
Nobuaki Soh , Selective Chemical Labeling of Proteins with Small Fluorescent Molecules Based on Metal-Chelation Methodology, Sensors 2008, 8, 1004-1024.*
English translation of Office Communication issued in Japanese Patent Application No. 2019-176325, dated Aug. 28, 2020.
GenBank Accession No. AAH15801, "PROS1 protein [*Homo sapiens*]," Aug. 11, 2006.
McDonald et al., "Ionic properties of membrane association by vitamin K-dependent proteins: The case for univalency," *Biochemistry*, 36:15589-15598, 1997.
Office Communication issued in New Zealand Patent Application No. 712058, dated Sep. 9, 2020.
Office Communication issued in New Zealand Patent Application No. 751491, dated Sep. 8, 2020.
Aaronson et al., "A Road Map for Those Who Don't Know JAK-STAT," Science, 296(5):1653-1655, 2002.
Abe et al., "Structural Analysis of the DF3 Human Breast Carcinoma-associated Protein," Cancer Research, 49(11):2834-2839, 1989.
Agata et al., "MUC1 Oncoprotein Blocks Death Recruitment of Caspase-8," Cancer Research, 68(15):6136-6144, 2008.
Ahmad et al., "MUCI oncoprotein activates the IκB kinase β complex and constitutive NF-κB signalling," Nature Cell Biology, 9(12):1419-1427, 2007.
Ahmad et al., "Triterpenoid CDDO-Me Blocks the NF-κB Pathway by Direct Inhibition of IKKβ on Cys-179," The Journal of Biological Chemistry, 281(4):35764-35769, 2006.

Ahmad et al., "Triterpenoid CDDO-Methyl Ester Inhibits the Janus-Activated Kinase-1 (JAK1) -->Signal Transducer and Activator of Transcription-3 (STAT3) Pathway by Direct Inhibition of JAK1 and STAT3," Cancer Research, 68(8):2920-2926, 2008.
Alvarez et al., "Identification of a Genetic Signature of Activated Signal Transducer and Activator of Transcription 3 in Human Tumors," Cancer Research, 65(12):5054-5062, 2005.
Alvarez et al., "Signal Transducer and Activator of Transcription 3 Is Required for the Oncogenic Effects of Non-Small-Cell Lung Cancer-Associated Mutations of the Epidermal Growth Factor Receptor," Cancer Research, 66(6):3162-3168, 2006.
Amara and Mercer, "Viral apoptotic mimicry," Nature Reviews Microbiology, 13(8)461-9, 2015.
Andaloussi et al., "Extracellular vesicles: Biology and emerging therapeutic opportunities," Nature Reviews Drug Discovery, 12(5):347-357, 2013.
Anderson et al., "Perspective—FcRn transports albumin: relevance to immunology and medicine," Trends in Immunology, 27(7):343-348, 2006.
Ashkenazi et al., "Immunoadhesins as research tools and therapeutic agents," Current Opinion in Immunology, 9:195-200, 1997.
Atoda et al., "Coagulation Factor X-Binding Protein from Deinagkistrodon acutus Venom Is a Gia Domain-Binding Protein," Biochemistry, vol. 37 (50), pp. 17361-17370, Nov. 25, 1998.
Baldus et al., "MUC1 and Nuclear β-Catenin Are Coexpressed at the Invasion Front of Colorectal Carcinomas and Are Both Correlated with Tumor Prognosis," Clinical Cancer Research, 10(8):2790-2796, 2004.
Beck et al., "Strategies and challenges for the next generation of antibody-drug conjugates," Nature Reviews Drug Discovery, 16(5):315-337, 2017.
Belhocine et al., "99mTc-Annexin A5 quantification of apoptotic tumor response: a systematic review and meta-analysis of clinical imaging trials," European Journal of Nuclear Medicine and Molecular Imaging, 42(13):2083-2097, 2015.
Belzile et al., "Antibody targeting of phosphatidylserine for the detection and immunotherapy of cancer," Immuno Targets and Therapy, 7:1014, 2018.
Benabdellah et al, "Genome-edited adult stem cells: Next-generation advanced therapy medicinal products," Stem Cells Translational Medicine, 9(6):674-685, 2020.
Birge et al., "Phosphatidylserine is a global immunosuppressive signal in efferocytosis, infectious disease, and cancer," Cell Death and Differentiation, 23(6):962-978, 2016.
Blankenberg, "Imaging the molecular signatures of apoptosis and injury with radiolabeled annexin V," Proceedings of the American Thoracic Society, vol. 6 (5), pp. 469-476, Aug. 15, 2009.
Bodanszky et al., "High Resolution Mass Spectra of Malformin and Related Cyclic Peptides," The Journal of Antibiotics, 29(5):549-553, 1976.
Boersma et al., "Past, Present, and Future of Annexin A5: From Protein Discovery to Clinical Applications," The Journal of Nuclear Medicine, 46(12):2035-2050, 2005.
Bowman et al., "STATs in oncogenesis," Oncogene, 19(21):2474-2488, 2000.
Brachert et al., "Compartmentalization of TNF Receptor 1 Signaling: Internalized TNF Receptosomes as Death Signaling Vesicles," Immunity, 21(3), pp. 415-428, 2004.
Bromberg et al., "Stat3 as an Oncogene," Cell, 98(3):295-303, 1999.
Buerger et al., "Sequence-specific Peptide Aptamers, Interacting with the Intracellular Domain of the Epidermal Growth Factor Receptor, Interfere with Stat3 Activation and Inhibit the Growth of Tumor Cells," The Journal of Biological Chemistry, 278(39):37610-37621, 2003.
Burstyn-Cohen and Maimon, "TAM receptors, phosphatidylserine, inflammation and cancer," Cell Communication and Signaling, 17(1):156, 2019.
Calianese and Birge, "Biology of phosphatidylserine (PS): basic physiology and implications in immunology, infectious disease and cancer," Communication and Signaling, 18(1):41, 2020.
Carter, "Potent antibody therapeutics by design," Nature Reviews Immunology, 6:343-357, 2006.

(56) References Cited

OTHER PUBLICATIONS

Chapman, "PEGylated antibodies and antibody fragments for improved therapy: a review," Advanced Drug Delivery Reviews, 54:531-545, 2002.

Chase, "Medical Applications of Radioisotopes," Remington's Pharmaceutical Sciences, 15th Ed., Mack Publishing Company, Easton, PA, Chapter 33, pp. 624-652, 1990.

Chaudhury et al., "The Major Histocompatibility Complex-related Fc Receptor for IgG (FcRn) Binds Albumin and Prolongs Its Lifespan," The Journal of Experimental Medicine, 197(3):315-322, 2003.

Chen et al., "Shaping the Nuclear Action of NFκB," Nature Reviews Molecular Cell Biology, 5:392-401, 2004.

Cohen et al., "From the Gla domain to a novel small-molecule detector of apoptosis," Cell Research, vol. 19(5), pp. 625-637, May 1, 2009.

Cohen et al., "Molecular Modeling Software and Methods for Medicinal Chemistry," Journal of Medicinal Chemistry, 33(3):883-894, 1990.

Colombo et al., "Biogenesis, Secretion, and Intercellular Interactions of Exosomes and Other Extracellular Vesicles," Annual Review of Cell and Developmental Biology, 30(1):255-289, 2014.

Conlan, "Early pathogenesis of Listeria monocytogenes infection in the mouse spleen," Journal o fMedical Microbiology, 44(4):295-302, 1996.

Crescitelli et al., "Distinct RNA profiles in subpopulations of extracellular vesicles: Apoptotic bodies, microvesicles and exosomes," Journal of Extracellular Vesicles, 2(1):2013.

Dahlbäck, "The tale of protein S and C4b-binding protein, a story of affection," Thrombosis and Haemostasis, 98(1):756-764, 2007.

Dayoub and Brekken, "TIMS, TAMS, and PS-antibody targeting: implications for cancer immunotherapy," Cell Communication and Signaling, 18(1):29, 2020.

Derose et al., "Development of bavituximab, a vascular targeting agent with immune-modulating properties, for lung cancer treatment," Immunotherapy, 3(8):933-944, 2011.

Dosio et al., "Immunotoxins and Anticancer Drug Conjugates Assemblies: The Role of the Linkage between Components," Toxins, 3:848-883, 2011.

Duraisamy et al., "Distinct evolution of the human carcinoma-associated transmembrane mucins, MUC1, MUC4 and MUC16," Gene, 373:28-34, 2006.

Duttaroy et al., "Development of a Long-Acting Insulin Analog Using Albumin Fusion Technology," Diabetes, 54:251-258, 2005.

Elliott et al., "Clearance of apoptotic cells: implications in health and disease," The Journal of Cell Biology, 189(7):1059-1070, 2010.

Elliott et al., "Enhancement of therapeutic protein in vivo activities through glycoengineering," Nature Biotechnology, 21:414-421, 2003.

Elliott et al., "Nucleotides released by apoptotic cells act as a find-me signal to promote phagocytic clearance," Nature, 461:282-286, 2009.

Elmore et al., "Apoptosis: A Review of Programmed Cell Death," Toxicol. Pathol., 29(6):997-1003, 2007.

Erwig et al., "Clearance of apoptotic cells by phagocytes," Cell Death and Differentiation, 15:243-250, 2008.

Extended European Search Report issued in European Patent Application No. 14770639.4, dated Jul. 28, 2016.

Extended European Search Report issued in European Patent Application No. 14769812.0, dated Aug. 1, 2016.

Fischer, "Cellular Uptake Mechanisms and Potential Therapeutic Utility of Peptidic Cell Delivery Vectors: Progress 2001-2006," Medicinal Research Reviews, 27(6):755-795, 2007.

Franklin, "Enzymes," Remington's Pharmaceutical Sciences, 18th Ed., Mack Publishing Company, Easton, PA, Chapter 52, pp. 1035-1038, 1990.

Gaemers et al., "A STAT-responsive Element in the Promoter of the Episialin/MUCI Gene Is Involved in Its Overexpression in Carcinoma Cells," The Journal of Biological Chemistry, 276(9):6191-6199, 2001.

Gendler et al., "A Highly Immunogenic Region of a Human Polymorphic Epithelial Mucin Expressed by Carcinomas Is Made Up of Tandem Repeats," The Journal of Biological Chemistry, 263(26):12820-12823, 1988.

Gerber et al., "Randomized phase III study of docetaxel plus bavituximab in previously treated advanced non-squamous non-small-cell lung cancer," Annals of Oncology, 29(7):1548-1553, 2018.

Germain et al., "Targeting the Cytoplasmic and Nuclear Functions of Signal Transducers and Activators of Transcription 3 for Cancer Therapy," Clinical Cancer Research, 13(19):5665-5669, 2007.

Gerondakis et al., "Unravelling the complexities of the NF-κB signalling pathway using mouse knockout and transgenic models," Oncogene, 25:6781-6799, 2006.

Ghetie et al., "Increasing the Serum Persistence of an IgG Fragment by Random Mutagenesis," Nature Biotechnology, 15:637-640, 1997.

Ghosh et al., "NF-Kappa B and Rel Proteins: Evolutionarily Conserved Mediators of Immune Responses," Annual Review of Immunology, 16:225-260, 1998.

Ghosh et al., "Rapid isolation of extracellular vesicles from cell culture and biological fluids using a synthetic peptide with specific affinity for heat shock proteins," PLoS ONE, 9(10):e110443, 2014.

Graner et al. "Tumor-derived exosomes, microRNAs, and cancer immune suppression," Seminars in Immunopathology, 40(5):505-515, 2018.

Grillot et al., "Genomic Organization, Promoter Region Analysis, and Chromosome Localization of the Mouse Bcl-X Gene," The Journal of Immunology, 158(10):4750-4757, 1997.

Gronenborn et al., "Protein Structure Determination in Solution by Two-Dimensional and Three-Dimensional Nuclear Magnetic Resonance Spectroscopy," Analytical Chemistry, 62(1):2-15, 1990.

Hansson and Stenflo, "Post-translational modifications in proteins involved in blood coagulation," J. Thrombosis Haemostasis, 3(12):2633-2648, 2005.

Hayden et al., "Shared Principles in NF-Kappab Signaling," Cell, 132(3):344-362, 2008.

Hemberger et al., "Trophoblast stem cells differentiate in vitro into invasive trophoblast giant cells," Developmental Biology, 271:362-371, 2004.

Hinton et al., "An Engineered Human IgG1 Antibody with Longer Serum Half-Life," Immunology, 176(1):346-356, 2006.

Hodel et al., "The Three-Dimensional Structure of the Autoproteolytic, Nuclear Pore-Targeting Domain of the Human Nucleoporin Nup98," Molecular Cell, (2):347-358, 2002.

Hoen et al., "Extracellular vesicles and viruses: Are they close relatives?" Proceedings of the National Academy of Sciences of the United States of America, 113(33):9155-9161, 2016.

Hoffmann et al., "Transcriptional Regulation via the NF-KappaB Signaling Module," Oncogene, 25(51):6706-671, 2006.

Huang and Lai, "The potential roles of stem cell-derived extracellular vesicles as a therapeutic tool," Annals of Translational Medicine, 7(22):693, 2019.

Huang et al., "MUC1 Cytoplasmic Domain Coactivates Wnt Target Gene Transcription and Confers Transformation," Cancer Biology & Therapy, 2(6):702-706, 2003.

Huang et al., "MUC1 Oncoprotein Blocks Glycogen Synthase Kinase 3beta-Mediated Phosphorylation and Degradation of Beta-Catenin," Cancer Research, 65(22):10413-10422, 2005.

Huang et al., "Structural basis of membrane binding by Gla domains of vitamin K-dependent proteins," Nature Structural Biology, vol. 10 (9), pp. 751-756, 2003.

Huxford et al., "The Crystal Structure of the IkappaBalpha/NF-KappaB Complex Reveals Mechanisms of NFKappaB Inactivation," Cell, vol. 95 (6), pp. 759-770, Dec. 11, 1998.

Jackson, "Contributions of Protein Structure-Based Drug Design to Cancer Chemotherapy," Seminars in Oncology, vol. 24 (2), pp. 164-172, Apr. 1997.

Jacobs et al., "Membrane Binding Properties of the Factor IX y-Carboxyglutamic Acid-rich Domain Prepared by Chemical Synthesis", The Journal of Biological Chemistry, vol. 269 (41), 25494-25501, Oct. 14, 1994.

Jacobs et al., "Structure of an IkappaBalpha/NF-KappaB Complex," Cell, vol. 95 (6), pp. 749-758, Dec. 11, 1998.

(56)          References Cited

OTHER PUBLICATIONS

Jain et al., "Engineering Antibodies for Clinical Applications," Trends in Biotechnology, vol. 25 (7), pp. 307-316, Jul. 2007.

Johnson et al., "Peptide Tum Mimetics," In: Biotechnology and Pharmacy, Chapter 14, Pezzuto J.M., et al., (Eds.,), Springer Science+ Business Media Dordrecht, NY, pp. 366-378, 1993.

Jones et al., "Structure-Based Design of Lipophilic Quinazoline Inhibitors of Thymidylate Synthase," Medicinal Chemistry, vol. 39 (4), pp. 904-917, Feb. 16, 1996.

Kanada et al., "Signaling by Extracellular Vesicles Advances Cancer Hallmarks," Trends in Cancer, 2(2):84-94, 2018.

Karin et al., "NF-kappaB at the Crossroads of Life and Death," Nature Immunology, vol. 3 (3), pp. 221-227, Mar. 2002.

Kau et al., "Nuclear Transport and Cancer: From Mechanism to Intervention," Nature Reviews Cancer, vol. 4 (2), pp. 106-117, Feb. 2004.

Kawano et al., "MUC1 Oncoprotein Regulates Bcr-Abl Stability and Pathogenesis in Chronic Myelogenous Leukemia Cells," Cancer Research, vol. 67 (24), pp. 11576-11584, Dec. 15, 2007.

Kenis et al., "Cell surface-expressed phosphatidylserine and annexin A5 open a novel portal of cell entry," J. Biol. Chemistry, 279(50):52623-52629, 2004.

Keyt et al., "A Faster-Acting and More Potent Form of Tissue Plasminogen Activator," Proceedings of the National Academy of Sciences, vol. 91 (9), pp. 3670-3674, Apr. 1994.

Kietselaer et al., "Molecular Imaging of Cell Death in Intracardiac Tumours: A New Approach to Differential Diagnosis in Cardiac Tumours," Netherlands Heart, vol. 10 (7-8), pp. 313-317, Aug. 2002.

Kinlough et al., "MUC1 Membrane Trafficking is Modulated by Multiple Interactions," Biological Chemistry, vol. 279 (51), p. 53071-53077, Dec. 17, 2004.

Kufe et al., "Differential Reactivity of a Novel Monoclonal Antibody (DF3) with Human Malignant Versus Benign Breast Tumors," Hybridoma, vol. 3 (3), pp. 223-232, 1984.

Kurihara et al., "Imaging and Dosimetry of 99mTc EC Annexin V: Preliminary Clinical Study Targeting Apoptosis in Breast Tumors," Applied Radiation and Isotopes, vol. 66 (9), pp. 1175-1182, 2008.

Lahorte et al., "Apoptosis-Detecting Radioligands: Current State of the Art and Future Perspectives," European Journal of Nuclear Medicine and Molecular Imaging, vol. 31 (6), pp. 887-919, Jun. 2004.

Lee et al., "Persistently Activated Stat3 Maintains Constitutive NF-kappab Activity in Tumors," Cancer Cell, vol. 15 (4), pp. 283-293, Apr. 7, 2009.

Lemke, "Phosphatidyleserine is the signal for TAM receptors and their ligands," Trends in Biochemical Sciences, 42(9):738-748, 2017.

Leng, et al., "Nuclear Import of the MUC1-C Oncoprotein is Mediated by Nucleoporin Nup62," Biological Chemistry, vol. 282 (27), pp. 19321-19330, Jul. 6, 2007.

Levitin et al., "The MUC1 SEA Module is a Self-Cleaving Domain," Biological Chemistry, vol. 280 (39), pp. 3337 4-33386, Sep. 30, 2005.

Levy et al., "Cellulose-Binding Domains: Biotechnological Applications," Biotechnology Advances, vol. 20 (3-4), pp. 191-213, Nov. 2002.

Li et al., "DF3/MUC1 Signaling In Multiple Myeloma Cells Is Regulated By Interleukin-7," Cancer Biology & Therapy, vol. 2 (2), pp. 187-193, Mar.-Apr. 2003.

Li et al., "Heregulin Targets Gamma-Catenin to the Nucleolus by a Mechanism Dependent on the DF3/MUC1 Oncoprotein," Molecular Cancer Research, vol. 1 (10), pp. 765-775, Aug. 2003.

Li et al., "Human DF3/MUC1 Carcinoma-Associated Protein Functions as an Oncogene," Oncogene, vol. 22 (38), pp. 6107-6110, Sep. 4, 2003.

Li et al., "Interaction of Glycogen Synthase Kinase 3bela with the DF3/MUC1 Carcinoma-Associated Antigen and Bela-Catenin," Molecular and Cellular Biology, vol. 18 (12), pp. 7216-7224, Dec. 1998.

Li et al., "Targeting phosphatidylserine with calcium-dependent protein-drug conjugates for the treatment of cancer," Molecular Cancer Therapeutics, 17(2):169-182, 2018.

Li et al., "The c-Src Tyrosine Kinase Regulates Signaling of the Human DF3/MUC1 Carcinoma-Associated Antigen with GSK3 Bela and Bela-Catenin," Biological Chemistry, vol. 276 (9), pp. 6061-6064, Mar. 2001.

Li et al., "The Epidermal Growth Factor Receptor Regulates Interaction of the Human DF3/MUC1 Carcinoma Antigen with C-Src and Bela-Catenin," Biological Chemistry, vol. 276 (38), pp. 35239-35242, Sep. 21, 2001.

Ligtenberg et al., "Cell-Associated Episialin Is a Complex Containing Two Proteins Derived From a Common Precursor," Biological Chemistry, vol. 267 (9), pp. 6171-6177, Mar. 25, 1992.

Lin et al., "Protein-Based Tumor Molecular Imaging Probes," Amino Acids, vol. 41 (5), pp. 1013-1036, Nov. 2011.

Loose et al., "[123]1-Inlerleukin-2 Uptake in Squamous Cell Carcinoma of the Head and Neck Carcinoma," European Journal of Nuclear Medicine and Molecular Imaging, vol. 35 (2), pp. 281-286, Feb. 2008.

Loose et al., "Prognostic Value of 99mTc-Hynic Annexin-V Imaging in Squamous Cell Carcinoma of the Head and Neck," European Journal of Nuclear Medicine and Molecular Imaging, vol. 35 (1), pp. 47-52, Jan. 2008.

Macao et al., "Autoproteolysis Coupled to Protein Folding in the SEA Domain of the Membrane-Bound MUC1 Mucin," Nature Structural & Molecular Biology, vol. 13 (1), pp. 71-76, Jan. 2006.

Mann et al., "Surface-dependent reactions of the vitamin K-dependent enzyme complexes," Journal of American Society of Hematology, 76:1-16, 1990.

McPherson, "Crystallization of Proteins From Polyethylene Glycol," Biological Chemistry, vol. 251 (20), pp. 6300-6303, Oct. 25, 1976.

Melder et al., "Pharmacokinetics and In Vitro and In Vivo Anti-Tumor Response of an Interleukin-2-Human Serum Albumin Fusion Protein in Mice," Cancer Immunology, Immunotherapy, vol. 54 (6), pp. 535-547, Jun. 2005.

Meerlo et al., "Frequent Alteration of the DF3 Tumor-Associated Antigen Gene in Primary Human Breast Carcinomas," Cancer Research, vol. 49 (24 Pt 1), pp. 6966-6971, Dec. 15, 1989.

Merrifield et al., "Solid Phase Peptide Synthesis. I. The Synthesis of a Tetrapeptide," American Chemical Society, vol. 85 (14), pp. 2149-2154, 1963.

Micheau et al., "Induction of TNF Receptor I-Mediated Apoptosis via Two Sequential Signaling Complexes," Cell, vol. 114 (2), pp. 181-190, Jul. 25, 2003.

Mille-Baker et al., "Deletion or replacement of the second EGF-like domain of protein S results in loss of APC cofactor activity," Blood, 101:1416-1418, 2003.

Mimura et al., "The Influence of Glycosylation on the Thermal Stability and Effector Function Expression of Human IgG1-Fc: Properties of a Series of Truncated Glycoforms," Molecular Immunology, vol. 37 (12-13), pp. 697-706, Aug.-Sep. 2000.

Murphy et al., "Extracellular vesicle-based therapeutics: natural versus engineered targeting and trafficking," Experimental and Molecular Medicine, 51(3):1-12, 2019.

Muthuswamy et al., "ErbB2, but not ErbB1, Reinitiates Proliferation and Induces Luminal Repopulation in Epithelial Acini," Nature Cell Biology, vol. 3 (9), pp. 785-792, Sep. 2001.

N'Guessan et al., "SapC-DOPS—a phosphatidylserine-targeted nanovesicle for selective cancer therapy," Cell Communication and Signaling, 18(6):2020.

Nakai et al., "A novel affinity-based method for the isolation of highly purified extracellular vesicles," Scientific Reports, 6(1):1-2, 2016.

Naresh et al., "Apoptosis Index Is a Predictor of Metastatic Phenotype in Patients with Early Stage Squamous Carcinoma of the Tongue: A Hypothesis to Support this Paradoxical Association," Cancer, vol. 91 (3), pp. 578-584, Feb. 1, 2001.

Natoli et al., "Interactions of NF-kappaB with Chromatin: The Art of Being at the Right Place at the Right Time," Nature Immunology, vol. 6 (5), pp. 439-445, May 2005.

(56) References Cited

OTHER PUBLICATIONS

Navia et al., "Use of Structural Information in Drug Design," Current Opinion in Structural Biology, vol. 2, pp. 202-210, 1992.

Nelsestuen, "Enhancement of Vitamin-K-Dependent Protein Function by Modification of the Gamma-Carboxyglutamic Acid Domain: Studies of Protein C and factor VII," Trends in Cardiovascular Medicine, vol. 9 (6), pp. 162-167, Aug. 1999.

Office Communication issued in Australian Patent Application No. 2014233885, dated Aug. 10, 2017.

Office Communication issued in Japanese Patent Application No. 2016-502002, dated Dec. 26, 2017. (English translation of Japanese text).

Office Communication issued in Japanese Patent Application No. 2016-502083, dated Feb. 20, 2018.

Office Communication issued in Russian Patent Application No. 2015144097, dated Dec. 15, 2017. (English translation of Russian text).

Office Communication issued in Singapore Patent Application No. 11201506307X, dated Oct. 3, 2017.

Office Communication issued in Singapore Patent Application No. 11201506880W, dated Dec. 28, 2017.

Office Communication issued in U.S. Appl. No. 14/772,971, dated Feb. 24, 2020.

Office Communication issued in U.S. Appl. No. 14/772,971, dated Aug. 9, 2019.

Office Communication issued in U.S. Appl. No. 14/772,971, dated Jan. 11, 2019.

Office Communication issued in U.S. Appl. No. 14/772,971, dated Jun. 29, 2018.

Office Communication issued in U.S. Appl. No. 14/772,971, dated Mar. 15, 2018.

Office Communication issued in U.S. Appl. No. 16/170,131, dated Feb. 27, 2020.

Office Communication issued in U.S. Appl. No. 16/170,131, dated Oct. 17, 2019.

Office Communication issued in U.S. Appl. No. 14/773,068, dated Nov. 29, 2016.

Office Communication issued in U.S. Appl. No. 14/773,068, dated Aug. 2, 2016.

Office Communication issued in U.S. Appl. No. 15/631,937, dated Jul. 25, 2018.

Office Communication issued in U.S. Appl. No. 15/631,937, dated Jan. 10, 2018.

Oguro et al., "SLAM family markers resolve functionally distinct subpopulations of hematopoietic stem cells and multipotent progenitors," Cell Stem Cell, 13:102-116, 2013.

Okada et al., "A novel splice site mutation in intron C of PROS1 leads to markedly reduced mutant mRNA level, absence of thrombin-sensitive region, and impaired secretion and cofactor activity of mutant protein S," Thrombosis Research, 125:e246-250, 2010.

Oling et al., "Trimers, dimers of trimers, and trimers of trimers are common building blocks of annexin A5 two-dimensional crystals," Journal of Structural Biology, 133(1):55-63, 2001.

Osborn et al., "Albutropin: A Growth Hormone-Albumin Fusion with Improved Pharmacokinetics and Dharmacodynamics in Rats and Monkeys," European Journal of Pharmacology, vol. 456 (1-3), pp. 149-158, Dec. 5, 2002.

Osborn et al., "Pharmacokinetic and Pharmacodynamic Studies of a Human Serum Albumin-Interferon-Alpha Fusion Protein in Cynomolgus Monkeys," Pharmacology and Experimental Therapeutics, vol. 303 (2), pp. 540-548, Nov. 2002.

Pasparakis et al., "Dissection of the NF-kappaB Signalling Cascade in Transgenic and Knockout Mice," Cell Death & Differentiation, vol. 13 (5), pp. 861-872, May 2006.

PCT International Preliminary Report on Patentability issued in International Application No. PCT/US2018/049618, dated Sep. 30, 2019.

PCT International Preliminary Report on Patentability issued in International Application No. PCT/US2018/049624, dated Jan. 10, 2020.

PCT International Search Report & Written Opinion issued in International Application No. PCT/US14/26237, dated Aug. 29, 2014.

PCT International Search Report and Written Opinion issued in International Patent Application No. PCT/US2014/025940, dated Jun. 27, 2014.

PCT International Search Report and Written Opinion issued in International Application No. PCT/US2018/049618, dated Dec. 6, 2018.

PCT International Search Report and Written Opinion issued in International Application No. PCT/US2018/049624, dated Dec. 5, 2018.

PCT International Search Report and Written Opinion issued in International Application No. PCT/US2018/049619, dated Dec. 6, 2018.

Percipalle et al., "Molecular Interactions between the Importin Alpha/Beta Heterodimer and Proteins Involved in Vertebrate Nuclear Protein Import," Molecular Biology, vol. 266 (4), pp. 722-732, Mar. 7, 1997.

Perey et al., "Effects of Differentiating Agents on Cell Surface Expression of the Breast Carcinoma-Associated DF3-P Epitope," Cancer Research, vol. 52 (22), pp. 6365-6370, Nov. 15, 1992.

Petkova et al., "Enhanced Half-Life of Genetically Engineered Human IgG1 Antibodies in a Humanized FcRn Mouse Model: Potential Application in Humorally Mediated Autoimmune Disease," International Immunology, vol. 18 (12), pp. 1759-1769, Dec. 2006.

Raina et al., "Direct Targeting of the Mucin 1 Oncoprotein Blocks Survival and Tumorigenicity of Human Breast Carcinoma Cells," Cancer Research, vol. 69 (12), pp. 5133-5141, Jun. 15, 2009.

Raina et al., "MUC1 Oncoprotein Blocks Nuclear Targeting of c-Abl in the apoptotic response to DNA damage," EMBO, 25:3774-3783, 2006.

Raina et al., "The MUC1 Oncoprotein Activates the Anti-Apoptotic Phosphoinositide 3-kinase/Akt and Bcl-xL Pathways in Rat 3y1 Fibroblasts," Biological Chemistry, vol. 279 (20), pp. 20607-20612, May 14, 2004.

Raju et al., "Fc Glycans Terminated with N-Acetylglucosamine Residues Increase Antibody Resistance to Dapain," Biotechnology Progress, vol. 23, pp. 964-971, 2007.

Raju et al., "Glycosylation in the Fe Domain of IgG Increases Resistance to Proteolytic Cleavage by Papain," Biochemical and Biophysical Research Communications, vol. 341 (3), pp. 797-803, Mar. 17, 2006.

Ramasamy et al., "The MUCI and Galectin-3 Oncoproteins Function in a MicroRNA-Dependent Regulatory Loop," Molecular Cell, vol. 27 (6), pp. 992-1004, Sep. 21, 2007.

Raposo and Stoorvogel, "Extracellular vesicles: exosomes, microvesicles, and friends," Journal of Cell Biology, 200(4):373-383, 2013.

Regan et al., "The Interaction between the Endothelial Cell Protein C Receptor and Protein C Is Dictated by the g-Carboxyglutamic Acid Domain of Protein C," The Journal of Biological Chemistry, vol. 272 (42), pp. 26279-26284, Oct. 17, 1976.

Ren et al., "Human MUC1 Carcinoma-Associated Protein Confers Resistance to Genotoxic Anticancer Agents," Cancer Cell, vol. 5 (2), pp. 163-175, Feb. 2004.

Ren et al., "Protein kinase C Delta Regulates Function of the DF3/MUC1 Carcinoma Antigen in Beta-Catenin Signaling," Biological Chemistry, vol. 277 (20), pp. 17616-17622, May 17, 2002.

Reutelingsperger et al., "Visualization of Cell Death in Vivo with the Annexin A5 imaging protocol," Immunological Methods, vol. 265 (1-2), pp. 123-132, Jul. 1, 2002.

Rezende et al., "Coagulation, inflammation, and apoptosis: Different roles for protein S and the protein S-C4b binding protein complex, Blood, 103(4):-1201, 2004.

Ryan et al., "The Nuclear Pore Complex: A Protein Machine Bridging the Nucleus and Cytoplasm," Current Opinion in Cell Biology, vol. 12 (3), pp. 361-371, Jun. 2000.

Schorey et al., "Exosomes and other extracellular vesicles in host-pathogen interactions," EMBO Reports, 16(1):24-43, 2015.

(56) References Cited

OTHER PUBLICATIONS

Schroeder et al., "MUC1 Overexpression Results in Mammary Gland Tumorigenesis and Prolonged Alveolar Differentiation," Oncogene, vol. 23 (34), pp. 5739-5747, Jul. 29, 2004.

Schroeder et al., "Transgenic MUC1 Interacts with Epidermal Growth Factor Receptor and Correlates with Mitogen-activated Protein Kinase Activation in the Mouse Mammary Gland," Biological Chemistry, vol. 276 (16), pp. 13057-13064, Apr. 20, 2001.

Schutters et al., "Phosphatidylserine targeting for diagnosis and treatment of human diseases," Apoptosis, vol. 15 (9), pp. 1072-1082, May 4, 2010.

Shah et al., "Manipulation of the Membrane Binding Site of Vitamin K-Dependent Proteins: Enhanced Biological Function of Human Factor VII," Proceedings of the National Academy of Sciences, vol. 95 (8), pp. 4229-4234, Apr. 14, 1998.

Shelke et al., "Importance of exosome depletion protocols to eliminate functional and RNA-containing extracellular vesicles from fetal bovine serum," Journal of Extracellular Vesicles, 3(1):2014.

Shlomovitz et al., "Flipping the dogma—phosphatidylserine in non-apoptotic cell death," Cell Communication and Signaling, 17(1):139, 2019.

Shuai et al., "Modulation of STAT Signaling by STAT-Interacting Proteins," Oncogene, vol. 19 (21), pp. 2638-2644, May 15, 2000.

Siddiquee et al., "Isolation and Sequencing of a CDNA Coding For the Human DF3 Breast Carcinoma-Associate Antigen," Proceedings of the National Academy of Sciences, vol. 85(7), pp. 2320-2323, Apr. 1988.

Siddiquee et al., "Selective Chemical Probe Inhibitor of Stat3, Identified Through Structure-Based Virtual Screening, Induces Anti-tumor Activity," Proceedings of the National Academy of Sciences, vol. 104 (18) pp. 7391-7396, May 1, 2007.

Sinclair et al., "Glycoengineering: The Effect of Glycosylation on the Properties of Therapeutic Proteins," Pharmaceutical Sciences, vol. 94 (8), pp. 1626-1635, Aug. 2005.

Soares et al., "Targeting Inside-Out Phosphatidylserine as a Therapeutic Strategy For Viral Diseases," Nat. Med., 14(12):1357-1362, 2008.

Song et al., "A Low-Molecular-Weight Compound Discovered Through Virtual Database Screening Inhibits stat3 Function In Breast Cancer Cells," Proceedings of the National Academy of Sciences, vol. 102 (13), pp. 4700-4705, Mar. 29, 2005.

Soule et al., "Isolation and Characterization Of A Spontaneously Immortalized Human Breast Epithelial Cell Line, MCF-10," Cancer Research, vol. 50 (18), pp. 6075-6086, Sep. 15, 1990.

Srivastava et al., "Localization of phosphatidylserine binding sites to structural domains of factor Xa," The Journal of Biological Chemistry, 277(3):1855-1863, 2002.

Stenflo, "Contributions of Gla and EGF-like domains to the function of vitamin K- dependent coagulation factors," Critical Reviews in Eukaryotic Gene Expression, 9(1):59-88, 1999.

Suh et al., "Translocation of B Catenin into the Nucleus Independent of Interactions with FG-Rich Nucleoporins," Experimental Cell Research, vol. 290, pp. 447-456, 2003.

Sung et al., "An IFN-Beta-Albumin Fusion Protein That Displays Improved Pharmacokinetic and Dharmacodynamic Properties in Nonhuman Primates," Interferon and Cytokine Research, vol. 23 (1), pp. 25-36, Jan. 2003.

Suzuki et al., "Xk-related protein 8 and CED-8 promote phosphtidylserine exposure in apoptotic cells," Science, 341(6144):403-406, 2013.

Tait et al., "Phospholipid Binding of Annexin V: Effects of Calcium and Membrane Phosphatidylserine Content," Archives of Biochemistry and Biophysics, vol. 298 (1), pp. 187-191, Oct. 1992.

Tietjen et al., "Molecular mechanism for differential recognition of membrane phosphtidylserine by the immune regulatory receptor Tim4," PNAS, 111(15):E1463-E1472, 2014.

Truscott et al., "A J-Protein Is an Essential Subunit of the Presequence Translocase-Associated Protein Import Motor of Mitochondria," The Journal of Cell Biology, vol. 163 (4), pp. 707-713, Nov. 24, 2003.

Turco, "Intravenous Admixtures", Mack Publishing Company, Easton, PA, Chapter 85, 1570-1580, 1990.

Umana et al., "Engineered Glycoforms of an Ant Neuroblastoma IgG1 with Optimized Antibody-Dependent Cellular Cytotoxic Activity," Nature Biotechnology, vol. 17 (2), pp. 176-180, Feb. 1999.

Vaccaro et al., "Engineering the Fc Region of Immunoglobulin G to Modulate in Vivo Antibody Levels," Nature Biotechnology, vol. 23 (10), pp. 1283-1288, Oct. 2005.

Valadi et al., "Exosome-mediated transfer of mRNAs and microRNAs is a novel mechanism of genetic exchange between cells," Nature Cell Biology, 9(6):654-659, 2007.

Van Den Eijnde et al., "Transient Expression of Phosphatidylserine at Cell-Cell Contact Areas is required for Myotube Formation," Journal of Cell Science, vol. 114 (PI 20), pp. 3631-3642, Oct. 2001.

Van Wijnen et al., "Characterization of mini-protein S, a recombinant variant of protein S that lacks the sex hormone binding globulin-like domain," Biochem. J., 330:389-396, 1998.

Vaupel and Multhoff, "Accomplices of hypoxic tumor microenvironment compromising antitumor immunity: adenosine, lactate, acidosis, vascular endothelial growth factor, potassium ions and phosphatidylserine," Frontiers in Immunology, 8:1887, 2017.

Vermeer et al., "Segregation of Receptor and Ligand Regulates Activation of Epithelial Growth Factor Receptor," Nature, vol. 422 (6929), pp. 322-326, Mar. 20, 2003.

Vermeer, "γ-Carboxyglutamate-containing proteins the vitamin K-dependent carboxylase," Biochemical Journal, 266:625-636, 1990.

Veronese et al., "PEGylalion, Successful Approach to Drug Delivery," Drug Discovery Today, vol. 10 (21), pp. 1451-1458, Nov. 1, 2005.

Wanderley et al., "Apoptotic mimicry as a strategy for the establishment of parasitic infections: parasite- and host-derived phosphtidylersine as key molecule," Cell Communication and Signaling, 18:10(1), 2020.

Wang et al. "SPECT and PET radiopharmaceuticals for molecular imaging of apoptosis: From bench to clinic," Oncotarget, 8(12):20479-20495, 2017.

Webb et al., "Vitamin K-Dependent Protein S Localizing Complement Regulator C4b-Binding Protein to the Surface of Apoptotic Cells," The Journal of Immunology, vol. 169 (5), pp. 2580-2586, Sep. 1, 2002.

Weber, "Physical Principles of Protein Crystallization," Advances in Protein Chemistry, vol. 41, pp. 1-36, 1991.

Wegenka et al., "The Inlerleukin-6-Aclivaled Acute-Phase Response Factor is Antigenically and Functionally Related to Members of the Signal Transducer and Activator of Transcription (STAT) family," Molecular and Cellular Biology, vol. 14 (5), pp. 3186-3196, May 1994.

Wei et al., "Human MUC1 Oncoprotein regulates p53-Responsive Gene Transcription in the Genotoxic Stress Response," Cancer Cell, vol. 7 (2), pp. 167-178, Feb. 2005.

Wei et al., "Human Mucin 1 Oncoprotein Represses Transcription of the p53 Tumor Suppressor Gene," Cancer Research, vol. 67 (4), pp. 1853-1858, Feb. 15, 2007.

Wei et al., "MUC1 Oncoprotein Stabilizes and Activates Estrogen Receptor Alpha," Molecular Cell, vol. 21 (2), pp. 295-305, Jan. 20, 2006.

Weis, "Regulating Access to the Genome: Nucleocytoplasmic Transport throughout the Cell Cycle," Cell, vol. 112 (4), pp. 441-451, Feb. 21, 2003.

Wen et al., "Nuclear Association of the Cytoplasmic Tail of MUC1 and Beta-Catenin," The Journal of Biological Chemistry, vol. 278 (39), pp. 38029-38039, Sep. 26, 2003.

Wider, "Structure Determination of Biological Macromolecules in Solution Using Nuclear Magnetic Resonance Spectroscopy," Biotechniques, vol. 29 (6), pp. 1278-1294, Dec. 2000.

Yamamoto et al., "Interaction of the DF3/MUC1 Breast Carcinoma-Associated Antigen and Beta-Catenin in Cell Adhesion," The Journal of Biological Chemistry, vol. 272 (19), pp. 12492-12494, May 9, 1997.

Yáñez-Mó et al. "Biological properties of extracellular vesicles and their physiological functions," Journal of Extracellular Vesicles, 14(4):2015.

(56) References Cited

OTHER PUBLICATIONS

Yeh et al., "Design of Yeast-Secreted Albumin Derivatives for Human Therapy: Biological and Antiviral Properties of a Serum Albumin-CD4 Genetic Conjugate," Proceedings of the National Academy of Sciences, USA, vol. 89 (5), pp. 1904-1908, Mar. 1, 1992.

Yin et al., "Human MUC1 Carcinoma Antigen Regulates Intracellular Oxidant Levels and the Apoptotic Response of Oxidative Stress," The Journal of Biological Chemistry, vol. 278 (37), pp. 35458-35464, Sep. 12, 2003.

Yin et al., "MUC1 Oncoprotein Activates the FOX03a Transcription Factor in a Survival Response to Oxidative Stress," The Journal of Biological Chemistry, vol. 279 (44), pp. 45721-45727, Oct. 29, 2004.

Yin et al., "Mucin 1 Oncoprotein Blocks Hypoxia-Inducible Factor lalpha Activation in a Survival Response to Hypoxia," The Journal of Biological Chemistry, vol. 282 (1), pp. 257-266, Jan. 5, 2007.

Young et al., "Molecular Chaperones Hsp90 and Hsp70 Deliver Preproteins to the Mitochondrial Import Receptor Tom70," Cell, vol. 112 (1), pp. 41-50, Jan. 10, 2003.

Yu et al., "Oncogenes as Regulators of Tissue Factor Expression in Cancer: Implications for Tumor Angiogenesis and Anti-Cancer Therapy," Seminars in Thrombosis and Hemostasis, vol. 30 (1), pp. 21-30, Feb. 2004.

Yu et al., "The STATs of Cancer—New Molecular Targets Come of Age," Nature Reviews Cancer, vol. 4 (2), pp. 97-105, Feb. 2004.

Zhang et al., "Interacting Regions in Stat3 and c-Jun that Participate in Cooperative Transcriptional Activation," Molecular and Cellular Biology, vol. 19 (10), pp. 7138-7146, Oct. 1999.

Yokoyama et al., "Immunohistochemical Detection of Phosphatidylserine and Thrombospondin on Denucleating Erythroblasts in Rat Bone Marrow", J. Vet. Med. Sci., 43:949-952, 2011.

Bhandari et al., "REX-1 expression and p38 MAPK activation status can determine proliferation/differentiation fates in human mesenchymal stem cells", PLoS One, 2010, vol. 5(5):e10493, 2010.

Guan et al., "Multiparameter characterization confirms apoptosis as the primary cause of reduced self-renewal capacity in cultured human fetal neural stem cells", Cellular Physiology and Biochemistry, 38(6):2123-2138, 2016.

Sebastian et al., Centrifugal countercurrent chromatography to elucidate surface differences of adipose tissue-derived stem cells, Journal of Separation Science, 35(10-11)1388-1398, 2012.

Hardy et al., "Gla-domain mediated targeting of externalized phosphatidylserine for intracellular delivery," FASEB J., 37(8), 2023.

Lai et al., "MSC secretes at least 3 EV types each with a unique permutation of membrane lipid, protein and RNA," Journal of extracellular vesicles, 5:29828, 2016.

Liang et al., "Development of a magnetic bead-based method for the collection of circulating extracellular vesicles," New Biotechnology, vol. 33, Issue No. 1: 116-122, 2016.

Zhu et al., "Hypoxia and serum deprivation-induced apoptosis in mesenchymal stem cells", Stem cells 24: 416-425, 2006.

Office Communication issued in Korean Patent Application No. 10-2020-7005896, dated Oct. 19, 2023. English Translation.

Office Communication issued in Korean Patent Application No. 10-2020-700278, dated Oct. 19, 2023. English Translation.

Skotland et al., "Lipids in exosomes: Current Knowledge and the way forward", Progress in Lipid Research, 66:30-41, 2017.

Xu et al., "Phosphatidylserine enhances osteogenic differentiation in human mesenchymal stem cells via ERK signal pathways", Materials Science and Engineering, 33:1783-1788, 2013.

Milsom, C. et al., "Tissue Factor and Cancer Stem Cells: Is There Linkage?", Arteriosclerosis, Thrombosis, and Vascular Biology, 29.12 (2009): 2005-2014.

* cited by examiner

| prep | | description |
|---|---|---|
| 1 | pEAKfl-CMV B0178 Gla+EGF | prothrombin signal sequence/propeptide |
| 2 | pEAKfl-CMV B0178 Gla | |
| 3 | pEAKfl-CMV B0178 Gla+EGF | |
| 4 | pEAKfl-CMV FVII Gla | |
| 5 | pEAKfl-CMV FVII Gla+EGF | |
| 6 | pEAKfl-CMV ProteinZ Gla | |
| 7 | pEAKfl-CMV ProteinZ Gla+EGF | |
| 8 | pEAKfl-CMV ProteinS Gla | |
| 9 | pEAKfl-CMV ProteinS Gla+EGF | |
| 10 | pEAKfl-CMV Prothrombin Gla | |
| 11 | pEAKfl-CMV Prothrombin Gla+Kringle | |

| Gla Protein | Gla domain only (kDa) | Gla+EGF/Kringle (kDa) |
|---|---|---|
| B0178 | 8.5 | 16.4 |
| FVII | 8.5 | 16.4 |
| Protein Z | 6.7 | 15.3 |
| Protein S | 8.4 | 28 |
| Prothrombin | 8.3 | 28.5 |

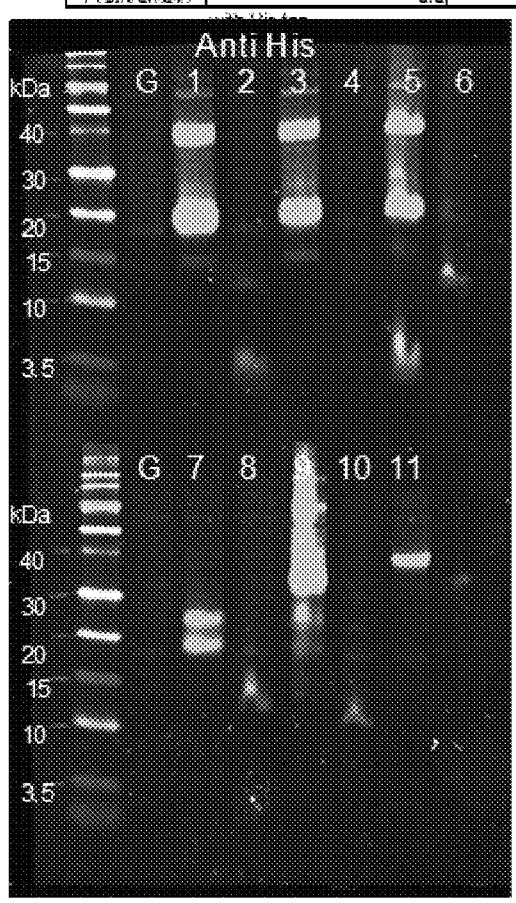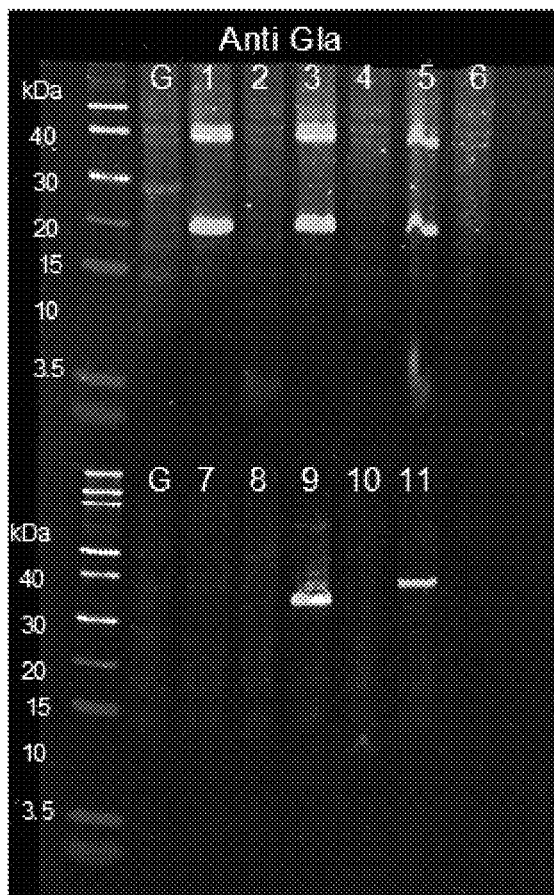

20ul of sample (1/100 of total cell pellet) loaded

| prep | description |
|---|---|
| 1 | pEAKfl-CMV B0178 Gla+EGF   prothrombin signal sequence/propeptide |
| 2 | pEAKfl-CMV B0178 Gla |
| 3 | pEAKfl-CMV B0178 Gla+EGF |
| 4 | pEAKfl-CMV FVII Gla |
| 5 | pEAKfl-CMV FVII Gla+EGF |
| 6 | pEAKfl-CMV ProteinZ Gla |
| 7 | pEAKfl-CMV ProteinZ Gla+EGF |
| 8 | pEAKfl-CMV ProteinS Gla |
| 9 | pEAKfl-CMV ProteinS Gla+EGF |
| 10 | pEAKfl-CMV Prothrombin Gla |
| 11 | pEAKfl-CMV Prothrombin Gla+Kringle |

FIG. 3

```
1           11          21          31          41          51          61          71
ANSLLSETKQ  GRLERECIEE  LCNEEAREV   FENDDPETDYF YFKDLVCLRS  FQTGLFTAAR  QSTRAYPDLR  SCVMAIPDQC
81          91          101         111         121         131         141         151
SDPCKNEDGT  MSCRDGKASF  TCTCRFGWQG  EKCEFDINEC  KDPSNINGGC  SQICDNTPGS  YHCSCNNGFV  MLSNKKDCKD
161         171         181         191         201         211         221         231
VDPCSIKFSI  CGTAVCKMIP  GDFECECPEG  YRYNLRSRSC  EDIDECSERM  CAQLCVNYPG  GYTCYCDGKK  GFELAQDQKS
241
CESRHHHHHH
```

PTMs:

γ-carboxylation: 11Gla
D95: hydroxylation
Disulfide bond: possible 14, reported 6
Tag: 6xHis

FIG. 5

Specificity of anti-His FITC antibody
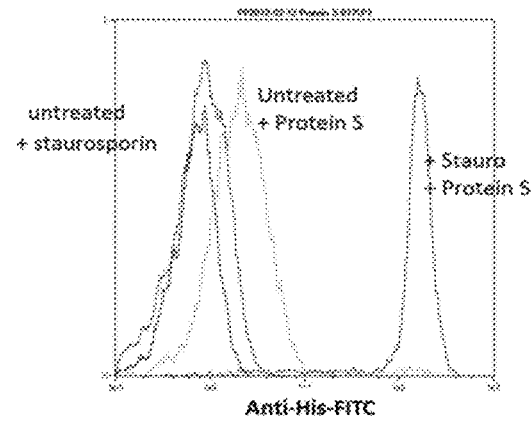
| ID | Untreated | + Stau | Untreated + Prot S | + Stau + Prot S |
|---|---|---|---|---|
| MFI | 0.91 | 0.79 | 4.72 | 159.3 |
Specificity of Annexin-FITC binding to apoptotic cells
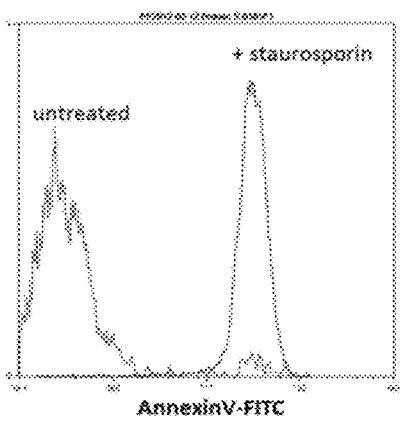
| ID | Untreated | + Stau |
|---|---|---|
| MFI | 1.93 | 32.3 |
Specificity of anti-His FITC antibody
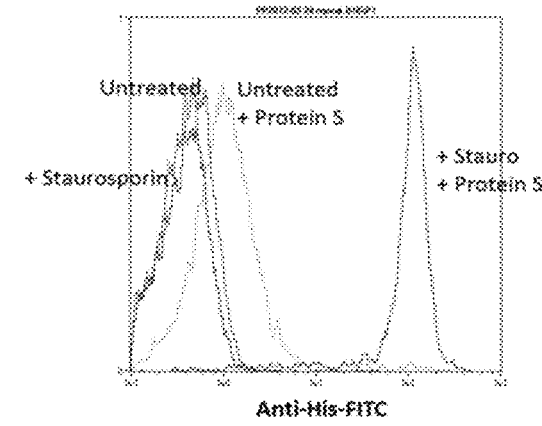
| ID | Untreated | + Stau | Untreated + Prot S | + Stau + Prot S |
|---|---|---|---|---|
| MFI | 0.38 | 0.38 | 3.23 | 109.5 |
Specificity of Annexin-FITC binding to apoptotic cells
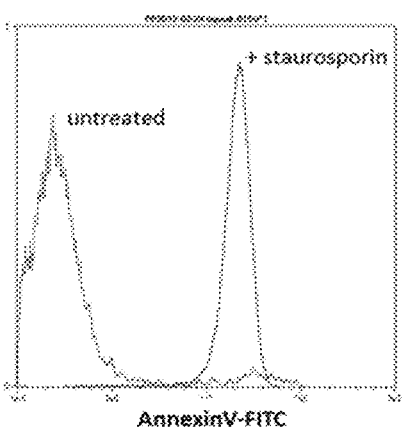
| ID | Untreated | + Stau |
|---|---|---|
| MFI | 1.89 | 21.9 |
FIG. 7

Annexin V competes off Protein S binding to Staurosporin treated Jurkat cells

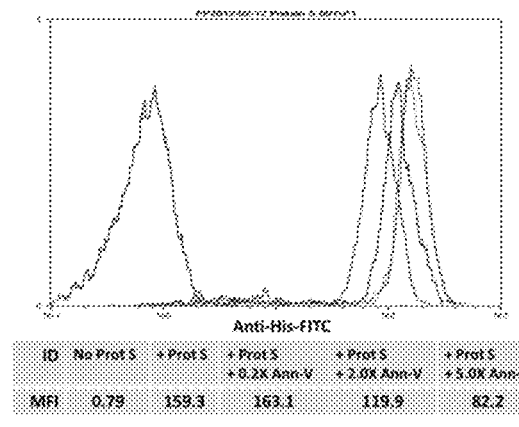

| ID | No Prot S | + Prot S | + Prot S<br>+ 0.2X Ann-V | + Prot S<br>+ 2.0X Ann-V | + Prot S<br>+ 5.0X Ann-V |
|---|---|---|---|---|---|
| MFI | 0.79 | 159.3 | 163.1 | 119.9 | 82.2 |

Weak binding of Protein S to untreated Jurkat is also competed off by Annexin V

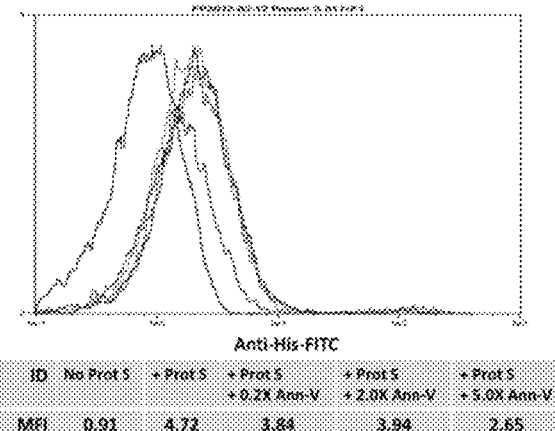

| ID | No Prot S | + Prot S | + Prot S<br>+ 0.2X Ann-V | + Prot S<br>+ 2.0X Ann-V | + Prot S<br>+ 5.0X Ann-V |
|---|---|---|---|---|---|
| MFI | 0.91 | 4.72 | 3.84 | 3.94 | 2.65 |

Annexin V competes off Protein S binding to Staurosporin treated Jurkat cells

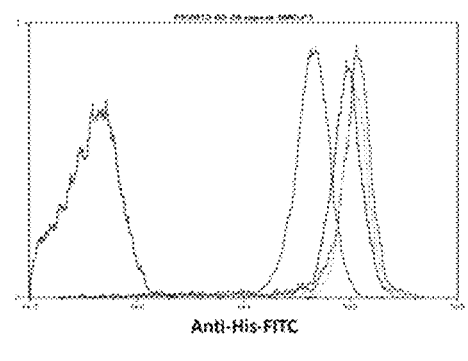

| ID | No Prot S | + Prot S | + Prot S<br>+ 0.4X Ann-V | + Prot S<br>+ 4.0X Ann-V | + Prot S<br>+ 10.0X Ann-V |
|---|---|---|---|---|---|
| MFI | 0.38 | 109.5 | 110.3 | 89.8 | 45.3 |

Weak binding of Protein S to untreated Jurkat is also competed off by Annexin V

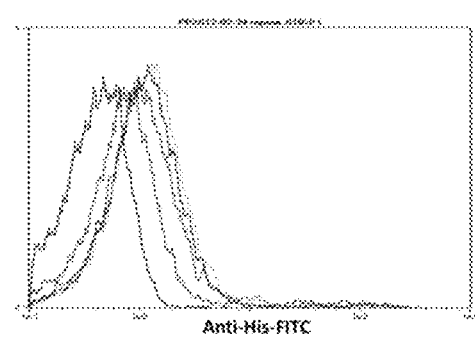

| ID | No Prot S | + Prot S | + Prot S<br>+ 0.4X Ann-V | + Prot S<br>+ 4.0X Ann-V | + Prot S<br>+ 10.0X Ann-V |
|---|---|---|---|---|---|
| MFI | 0.38 | 3.23 | 2.52 | 2.86 | 2.32 |

FIG. 8

SEQUENCE LISTING

<160> NUMBER OF SEQ ID NOS: 6

<210> SEQ ID NO 1
<211> LENGTH: 45
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<222> LOCATION: (6)..(7)
<223> OTHER INFORMATION: Xaa is gamma-carboxyglutamic acid residue
<220> FEATURE:
<221> NAME/KEY: MISC_FEATURE
<222> LOCATION: (14)..(14)
<223> OTHER INFORMATION: Xaa is gamma-carboxyglutamic acid residue
<220> FEATURE:
<221> NAME/KEY: MISC_FEATURE
<222> LOCATION: (16)..(16)
<223> OTHER INFORMATION: Xaa is gamma-carboxyglutamic acid residue
<220> FEATURE:
<221> NAME/KEY: MISC_FEATURE
<222> LOCATION: (19)..(20)
<223> OTHER INFORMATION: Xaa is gamma-carboxyglutamic acid residue
<220> FEATURE:
<221> NAME/KEY: MISC_FEATURE
<222> LOCATION: (25)..(26)
<223> OTHER INFORMATION: Xaa is gamma-carboxyglutamic acid residue
<220> FEATURE:
<221> NAME/KEY: MISC_FEATURE
<222> LOCATION: (29)..(29)
<223> OTHER INFORMATION: Xaa is gamma-carboxyglutamic acid residue
<220> FEATURE:
<221> NAME/KEY: MISC_FEATURE
<222> LOCATION: (32)..(32)
<223> OTHER INFORMATION: Xaa is gamma-carboxyglutamic acid residue
<220> FEATURE:
<221> NAME/KEY: MISC_FEATURE
<222> LOCATION: (36)..(36)
<223> OTHER INFORMATION: Xaa is gamma-carboxyglutamic acid residue

<400> SEQUENCE: 1

Ala Asn Ser Leu Leu Xaa Xaa Thr Lys Gln Gly Asn Leu Xaa Arg Xaa
1               5                   10                  15

Cys Ile Xaa Xaa Leu Cys Asn Lys Xaa Xaa Ala Arg Xaa Val Phe Xaa
            20                  25                  30

Asn Asp Pro Xaa Thr Asp Tyr Phe Tyr Pro Lys Tyr Leu
        35                  40                  45

<210> SEQ ID NO 2
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(8)
<223> OTHER INFORMATION: Xaa is gamma-carboxyglutamic acid residue
<220> FEATURE:
<221> NAME/KEY: MISC_FEATURE
<222> LOCATION: (11)..(11)
<223> OTHER INFORMATION: Xaa is gamma-carboxyglutamic acid residue
<220> FEATURE:
<221> NAME/KEY: MISC_FEATURE
<222> LOCATION: (15)..(15)
<223> OTHER INFORMATION: Xaa is gamma-carboxyglutamic acid residue
<220> FEATURE:
<221> NAME/KEY: MISC_FEATURE
<222> LOCATION: (17)..(17)
<223> OTHER INFORMATION: Xaa is gamma-carboxyglutamic acid residue
<220> FEATURE:
<221> NAME/KEY: MISC_FEATURE
<222> LOCATION: (20)..(21)
<223> OTHER INFORMATION: Xaa is gamma-carboxyglutamic acid residue
<220> FEATURE:
<221> NAME/KEY: MISC_FEATURE
<222> LOCATION: (26)..(27)
<223> OTHER INFORMATION: Xaa is gamma-carboxyglutamic acid residue
<220> FEATURE:
<221> NAME/KEY: MISC_FEATURE
<222> LOCATION: (30)..(30)
<223> OTHER INFORMATION: Xaa is gamma-carboxyglutamic acid residue
```

```
<220> FEATURE:
<221> NAME/KEY: MISC_FEATURE
<222> LOCATION: (33)..(33)
<223> OTHER INFORMATION: Xaa is gamma-carboxyglutamic acid residue
<220> FEATURE:
<221> NAME/KEY: MISC_FEATURE
<222> LOCATION: (35)..(35)
<223> OTHER INFORMATION: Xaa is gamma-carboxyglutamic acid residue
<220> FEATURE:
<221> NAME/KEY: MISC_FEATURE
<222> LOCATION: (40)..(40)
<223> OTHER INFORMATION: Xaa is gamma-carboxyglutamic acid residue

<400> SEQUENCE: 2

Ala Gly Ser Tyr Leu Leu Xaa Xaa Leu Phe Xaa Gly Asn Leu Xaa Lys
1               5                   10                  15

Xaa Cys Tyr Xaa Xaa Ile Cys Val Tyr Xaa Xaa Ala Arg Xaa Val Phe
            20                  25                  30

Xaa Asn Xaa Val Val Thr Asp Xaa Phe Trp Arg Arg Tyr Lys
        35                  40                  45

<210> SEQ ID NO 3
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(7)
<223> OTHER INFORMATION: Xaa is gamma-carboxyglutamic acid residue
<220> FEATURE:
<221> NAME/KEY: MISC_FEATURE
<222> LOCATION: (14)..(14)
<223> OTHER INFORMATION: Xaa is gamma-carboxyglutamic acid residue
<220> FEATURE:
<221> NAME/KEY: MISC_FEATURE
<222> LOCATION: (16)..(16)
<223> OTHER INFORMATION: Xaa is gamma-carboxyglutamic acid residue
<220> FEATURE:
<221> NAME/KEY: MISC_FEATURE
<222> LOCATION: (19)..(20)
<223> OTHER INFORMATION: Xaa is gamma-carboxyglutamic acid residue
<220> FEATURE:
<221> NAME/KEY: MISC_FEATURE
<222> LOCATION: (25)..(26)
<223> OTHER INFORMATION: Xaa is gamma-carboxyglutamic acid residue
<220> FEATURE:
<221> NAME/KEY: MISC_FEATURE
<222> LOCATION: (29)..(29)
<223> OTHER INFORMATION: Xaa is gamma-carboxyglutamic acid residue
<220> FEATURE:
<221> NAME/KEY: MISC_FEATURE
<222> LOCATION: (32)..(32)
<223> OTHER INFORMATION: Xaa is gamma-carboxyglutamic acid residue

<400> SEQUENCE: 3

Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
            20                  25                  30

Ser Ser Thr Ala Thr Asp Val Phe Trp Ala Lys Tyr Thr
        35                  40                  45

<210> SEQ ID NO 4
<211> LENGTH: 45
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (6)..(7)
<223> OTHER INFORMATION: Xaa is gamma-carboxyglutamic acid residue
<220> FEATURE:
<221> NAME/KEY: MISC_FEATURE
<222> LOCATION: (14)..(14)
<223> OTHER INFORMATION: Xaa is gamma-carboxyglutamic acid residue
<220> FEATURE:
<221> NAME/KEY: MISC_FEATURE
<222> LOCATION: (16)..(16)
<223> OTHER INFORMATION: Xaa is gamma-carboxyglutamic acid residue
<220> FEATURE:
<221> NAME/KEY: MISC_FEATURE
<222> LOCATION: (19)..(20)
<223> OTHER INFORMATION: Xaa is gamma-carboxyglutamic acid residue
<220> FEATURE:
<221> NAME/KEY: MISC_FEATURE
<222> LOCATION: (25)..(26)
<223> OTHER INFORMATION: Xaa is gamma-carboxyglutamic acid residue
<220> FEATURE:
<221> NAME/KEY: MISC_FEATURE
<222> LOCATION: (29)..(29)
<223> OTHER INFORMATION: Xaa is gamma-carboxyglutamic acid residue
<220> FEATURE:
<221> NAME/KEY: MISC_FEATURE
<222> LOCATION: (35)..(35)
<223> OTHER INFORMATION: Xaa is gamma-carboxyglutamic acid residue

<400> SEQUENCE: 4

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser
        35                  40                  45

<210> SEQ ID NO 5
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(7)
<223> OTHER INFORMATION: Xaa is gamma-carboxyglutamic acid residue
<220> FEATURE:
<221> NAME/KEY: MISC_FEATURE
<222> LOCATION: (14)..(14)
<223> OTHER INFORMATION: Xaa is gamma-carboxyglutamic acid residue
<220> FEATURE:
<221> NAME/KEY: MISC_FEATURE
<222> LOCATION: (16)..(16)
<223> OTHER INFORMATION: Xaa is gamma-carboxyglutamic acid residue
<220> FEATURE:
<221> NAME/KEY: MISC_FEATURE
<222> LOCATION: (19)..(20)
<223> OTHER INFORMATION: Xaa is gamma-carboxyglutamic acid residue
<220> FEATURE:
<221> NAME/KEY: MISC_FEATURE
<222> LOCATION: (25)..(26)
<223> OTHER INFORMATION: Xaa is gamma-carboxyglutamic acid residue
<220> FEATURE:
<221> NAME/KEY: MISC_FEATURE
<222> LOCATION: (29)..(29)
<223> OTHER INFORMATION: Xaa is gamma-carboxyglutamic acid residue
<220> FEATURE:
<221> NAME/KEY: MISC_FEATURE
<222> LOCATION: (32)..(32)
<223> OTHER INFORMATION: Xaa is gamma-carboxyglutamic acid residue
<220> FEATURE:
<221> NAME/KEY: MISC_FEATURE
<222> LOCATION: (35)..(35)
<223> OTHER INFORMATION: Xaa is gamma-carboxyglutamic acid residue
```

```
<400> SEQUENCE: 5

Ala Asn Ala Phe Leu Xaa Xaa Leu Arg Gln Gly Ser Leu Xaa Arg Xaa
1               5                   10                  15

Cys Lys Xaa Xaa Gln Cys Ser Phe Xaa Xaa Ala Arg Xaa Ile Phe Xaa
            20                  25                  30

Asp Ala Xaa Arg Thr Lys Leu Phe Trp Ile Ser Tyr Ser
            35                  40                  45

<210> SEQ ID NO 6
<211> LENGTH: 250
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(7)
<223> OTHER INFORMATION: Xaa is gamma-carboxyglutamic acid residue
<220> FEATURE:
<221> NAME/KEY: MISC_FEATURE
<222> LOCATION: (14)..(14)
<223> OTHER INFORMATION: Xaa is gamma-carboxyglutamic acid residue
<220> FEATURE:
<221> NAME/KEY: MISC_FEATURE
<222> LOCATION: (16)..(16)
<223> OTHER INFORMATION: Xaa is gamma-carboxyglutamic acid residue
<220> FEATURE:
<221> NAME/KEY: MISC_FEATURE
<222> LOCATION: (19)..(20)
<223> OTHER INFORMATION: Xaa is gamma-carboxyglutamic acid residue
<220> FEATURE:
<221> NAME/KEY: MISC_FEATURE
<222> LOCATION: (25)..(26)
<223> OTHER INFORMATION: Xaa is gamma-carboxyglutamic acid residue
<220> FEATURE:
<221> NAME/KEY: MISC_FEATURE
<222> LOCATION: (29)..(29)
<223> OTHER INFORMATION: Xaa is gamma-carboxyglutamic acid residue
<220> FEATURE:
<221> NAME/KEY: MISC_FEATURE
<222> LOCATION: (32)..(32)
<223> OTHER INFORMATION: Xaa is gamma-carboxyglutamic acid residue
<220> FEATURE:
<221> NAME/KEY: MISC_FEATURE
<222> LOCATION: (36)..(36)
<223> OTHER INFORMATION: Xaa is gamma-carboxyglutamic acid residue

<400> SEQUENCE: 6

Ala Asn Ser Leu Leu Xaa Xaa Thr Lys Gln Gly Asn Leu Xaa Arg Xaa
1               5                   10                  15

Cys Ile Xaa Xaa Leu Cys Asn Lys Xaa Xaa Ala Arg Xaa Val Phe Xaa
            20                  25                  30

Asn Asp Pro Xaa Thr Asp Tyr Phe Tyr Pro Lys Tyr Leu Val Cys Leu
            35                  40                  45

Arg Ser Phe Gln Thr Gly Leu Phe Thr Ala Ala Arg Gln Ser Thr Asn
    50                  55                  60

Ala Tyr Pro Asp Leu Arg Ser Cys Val Asn Ala Ile Pro Asp Gln Cys
65                  70                  75                  80

Ser Pro Leu Pro Cys Asn Glu Asp Gly Tyr Met Ser Cys Lys Asp Gly
                85                  90                  95

Lys Ala Ser Phe Thr Cys Thr Cys Lys Pro Gly Trp Gln Gly Glu Lys
                100                 105                 110

Cys Glu Phe Asp Ile Asn Glu Cys Lys Asp Pro Ser Asn Ile Asn Gly
        115                 120                 125

Gly Cys Ser Gln Ile Cys Asp Asn Thr Pro Gly Ser Tyr His Cys Ser
        130                 135                 140
```

```
Cys Lys Asn Gly Phe Val Met Leu Ser Asn Lys Lys Asp Cys Lys Asp
145             150             155             160

Val Asp Glu Cys Ser Leu Lys Pro Ser Ile Cys Gly Thr Ala Val Cys
                165             170             175

Lys Asn Ile Pro Gly Asp Phe Glu Cys Glu Cys Pro Glu Gly Tyr Arg
            180             185             190

Tyr Asn Leu Lys Ser Lys Ser Cys Glu Asp Ile Asp Glu Cys Ser Glu
        195             200             205

Asn Met Cys Ala Gln Leu Cys Val Asn Tyr Pro Gly Gly Tyr Thr Cys
    210             215             220

Tyr Cys Asp Gly Lys Lys Gly Phe Lys Leu Ala Gln Asp Gln Lys Ser
225             230             235             240

Cys Glu Ser Arg His His His His His His
            245             250
```

GLA DOMAINS AS THERAPEUTIC AGENTS

This application is a continuation application of U.S. patent application Ser. No. 16/170,131, filed Oct. 25, 2018, which is a continuation of U.S. patent application Ser. No. 15/631,937, filed Jun. 23, 2017, now abandoned, which is a continuation application of U.S. patent application Ser. No. 14/773,068, now U.S. Pat. No. 9,694,048, which adopts the international filing date of Mar. 13, 2014, which is the National Phase application under 35 U.S.C. § 371 of International Application No. PCT/US2014/26237, filed Mar. 13, 2014, which claims the benefit of priority to U.S. Provisional Application Ser. No. 61/791,537 filed Mar. 15, 2013, and U.S. Provisional Application Ser. No. 61/787,753, filed Mar. 15, 2013, the disclosures of each of which are hereby incorporated by reference in their entireties for all purposes.

Pursuant to 37 C.F.R. 1.821(c), a sequence listing is submitted herewith as an ASCII compliant text file named "STIPP0003USC3_ST25.txt", created on Sep. 14, 2020 and having a size of ~10 kilobytes. The content of the aforementioned file is hereby incorporated by reference in its entirety.

BACKGROUND

1. Field

This disclosure relates to the targeting of phosphatidylserine (PtdS) on cell membranes using Gla domain peptides and polypeptides. The use of these peptides and polypeptides as therapeutic agents is disclosed.

2. Related Art

Phosphatidlyserine (PtdS) is a negatively charged phospholipid component usually localized to the inner-leaflet (the cytoplasmic side) of the cell membrane. However, PtdS can be transported by scramblase (a member of the flippase family) from the inner-leaflet to the outer-leaflet and exposed on the cell surface. With very few exceptions, this active externalization of PtdS is a response to cellular damage (van den Eijnde et al., 2001; Erwig and Henson, 2008). For example, tissue injury signals platelets, leukocytes, and endothelial cells to rapidly and reversibly redistribute PtdS which leads to the promotion of coagulation and complement activation on cell surfaces. Similarly, apoptotic signals result in the externalization of PtdS however in a more gradual and sustained manner. This external PtdS provides a key recognition marker that enables macrophages to ingest dying cells from surrounding tissue while suppressing a full and detrimental immune response (Erwig and Henson, 2008). This removal process is essential for tissue homeostasis and in a "healthy" environment it is extremely efficient. In fact, despite the loss of >10⁹ cells per day, the histological detection of apoptotic cells is a rare event in normal tissues (Elltiot and Ravichandran, 2010; Elltiot et al., 2009). However, there is evidence that in many pathological conditions the process of apoptotic cell removal is overwhelmed, delayed or absent (Elltiot and Ravichandran, 2010; Lahorte et al., 2004). For example, several oncology studies suggest that a high apoptotic index is associated with higher grade tumors, increased rate of metastasis and a poor prognosis for the patient (Naresh et al., 2001; Loose et al., 2007; Kurihara et al., 2008; Kietselaer et al., 2002). These studies, and others like them, suggest that apoptosis and external PtdS expression can be a powerful marker of disease (Elltiot and Ravichandran, 2010).

There are several proteins with a high affinity for anionic phospholipid surfaces with Annexin-V being the most widely utilized as a PtdS targeting probe (Lahorte et al., 2004). With a high affinity for PtdS containing vesicles ($K_d$=0.5-7 nM) and a molecular weight (37 kDa) that falls below the threshold for kidney filtration (approx. 60 kDa) Annexin-V has shown promise in the clinic as an apoptosis-probe (Lin et al., 2010; Tait and Gibson, 1992). Moreover, it has been utilized for a wide range of indications including those in oncology, neurology and cardiology (Lahorte et al., 2004; Boersma et al., 2005; Blankenberg, 2009; Reutelingsperger et al., 2002). The use of biologic probes which target PtdS cell-surface expression has been shown both in vitro and in vivo. While their utility in the clinic is promising, they have, for the most part, not yet been exploited.

SUMMARY

Thus, in accordance with the present disclosure, there is provided a method of targeting cell membrane phosphatidylserine (PtdS) comprising (a) providing an isolated polypeptide comprising a gamma-carboxyglutamic-acid (Gla) domain and lacking a protease or hormone-binding domain; and (b) contacting the peptide with a cell surface, wherein the polypeptide binds to PtdS on the cell membrane. The cell membrane may be a cardiac cell membrane, a neuronal cell membrane, an endothelial cell membrane, a virus-infected cell membrane, an apoptotic cell membrane, a platelet membrane, a plasma membrane-derived veriscle (PMV) or a cancer cell membrane. The polypeptide may further comprise an EGF binding domain, a Kringle domain, and/or an aromatic amino acid stack domain. The Gla domain may be from Factor II, Factor VII, Factor IX, Factor X, protein S or protein C. The polypeptide may further comprise a detectable label, such as a fluorescent label, a chemilluminescent label, a radiolabel, an enzyme, a dye or a ligand.

The polypeptide may be 300 residues or less, 200 residues or less, or 100 residues or less, including ragnes of 100-200 and 100-300 residues. The polypeptide may comprise 5-15 Gla residues, 9-13 Gla residues, including 5, 6, 7, 8, 9, 10, 11, 12, 13, 14, or 15 Gla residues. The polypeptide may comprise more than 13 Gla residues, but less than 30% total Gla residues. The polypeptide may be between about 4.5 and 30 kD in size. The polypeptide may comprise at least one disulfide bond, or 2-5 disulfide bonds. The polypeptide may comprise a protein S Gla domain. The polypeptide may comprise a protein S Gla domain, a protein S EGF domain, a prothrombin Gla domain, a prothrombin Gla domain plus prothrombin Kringle domain, a protein Z Gla domain, a protein Z Gla domain plus prothrombin Kringle domain, a Factor VII Gla domain, or a Factor VII Gla domain plus prothrombin Kringle domain. The polypeptide may further comprise an antibody Fc region. Any of the foregoing may contain conservative substitutions of the native sequences for the foregoing proteins, and/or exhibit a percentage homology to the native domains set forth.

In another embodiment, there is provided a method of treating cancer in a subject comprising administering to the subject an isolated polypeptide comprising a gamma-carboxyglutamic-acid (Gla) domain and lacking a protease or hormone-binding domain. The cancer may be breast cancer, brain cancer, stomach cancer, lung cancer, prostate cancer, ovarian cancer, testicular cancer, colon cancer, skin cancer, rectal cancer, cervical cancer, uterine cancer, liver cancer, pancreatic cancer, head & neck cancer or esophageal cancer. The method may further comprise treating the subject with a second cancer therapy, such as an immunotherapy, a radiotherapy, a chemotherapy, a toxin therapy, a cytokine therapy or a hormone therapy.

Yet another embodiment includes a method of treating an autoimmune disease in a subject comprising administering to the subject an isolated polypeptide comprising a gamma-carboxyglutamic-acid (Gla) domain and lacking a protease or hormone-binding domain. The autoimmune disease may be spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, systemic lupus erythematosus, psoriasis, vasculitis, Wegener's granulomatosis, Addison's disease, alopecia, antiphospholipid syndrome, Behcet's disease, celiac disease, chronic fatigue syndrome, ulcerative colitis, type I diabetes, fibromyalgia, autoimmune gastritis, Goodpasture syndrome, Graves' disease, idiopathic thrombocytopenic purpura (ITP), myasthenia gravis, pemphigus vulgaris, primary biliary cirrhosis, rheumatic fever, sarcoidosis, scleroderma, vitiligo, vasculitis, small vessel vasculitis, hepatitis, primary biliary cirrhosis, sarcoidosis, scleroderma, graft versus host disease (acute and chronic), aplastic anemia, or cyclic neutropenia. The method may further comprise treating the subject with a second autoimmune disease therapy, such as prednisone, methylprednisone, Venipred, Celestone, hydrocortisone, triamcinoclone, Aristonpan Intra-Articular injection, Methapred, Rayos oral, betamethasone, or etanercept.

In still another embodiment, there is provided a method of treating a viral disease in a subject comprising administering to the subject an isolated polypeptide comprising a gamma-carboxyglutamic-acid (Gla) domain and lacking a protease or hormone-binding domain. The viral disease may be influenza, human immunodeficiency virus, dengue virus, West Nile virus, smallpox virus, respiratory syncytial virus, Korean hemorrhagic fever virus, chickenpox, varicella zoster virus, herpes simplex virus 1 or 2, Epstein-Barr virus, Marburg virus, hantavirus, yellow fever virus, hepatitis A, B, C or E, Ebola virus, human papilloma virus, rhinovirus, Coxsackie virus, polio virus, measles virus, rubella virus, rabies virus, Newcastle disease virus, rotavirus, HTLV-1 and -2. The method may further comprise treating the subject with a second anti-viral therapy, such as Abacavir, Aciclovir, Acyclovir, Adefovir, Amantadine, Amprenavir, Ampligen, Arbidol, Atazanavir, Atripla, Bocepreviretet, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Stavudine, Synergistic enhancer (antiretroviral), Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir or Zidovudine.

In still a further embodiment, there is provided a method of treating a hypercoagulation disorder in a subject comprising administering to the subject an isolated polypeptide comprising a gamma-carboxyglutamic-acid (Gla) domain and lacking a protease or hormone-binding domain. The method may further comprise treating the subject with one or more additional anti-coagulants.

Also provided are methods of modulating clotting in a subject comprising administering to the subject an isolated polypeptide comprising a gamma-carboxyglutamic-acid (Gla) domain and lacking a protease or hormone-binding domain. The method may further comprise administering to the subject a clotting factor.

Yet another embodiment comprises treating sepsis in a subject comprising administering to the subject an isolated polypeptide comprising a gamma-carboxyglutamic-acid (Gla) domain and lacking a protease or hormone-binding domain. A still further embodiment includes a method of treating vaso-occlusive crisis in a sickle cell subject comprising administering to the subject an isolated polypeptide comprising a gamma-carboxyglutamic-acid (Gla) domain and lacking a protease or hormone-binding domain.

Finally, there is provided a method treating a disorder characterized by pathologic expression of phosphatidylserine on the surface of a cell comprising administering to the subject an isolated polypeptide comprising a gamma-carboxyglutamic-acid (Gla) domain and lacking a protease or hormone-binding domain.

It is contemplated that any method or composition described herein can be implemented with respect to any other method or composition described herein.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed.

FIG. 3—Testing of Gla domain protein constructs for expression. Transient transfection in BHK21 cells. 10% gels with reduced samples, 20 µl (1/100 total cell pellet) loaded.

FIG. 5—Protein S Gla+EGF sequence. Sequence is SEQ ID NO: 6.

FIG. 7—Apoptosis Assays for Protein S Gla+EGF. Top and bottom panels represent identical duplicate procedures except that amounts of Protein S Gla+EGF was reduced, and the amount of anti-His domain antibody was reduced.

FIG. 8—Apoptosis Assays for Protein S Gla+EGF. Top and bottom panels represent identical duplicate procedures except for amounts of Annexin V used, which are double in the bottom panels.

DESCRIPTION OF ILLUSTRATIVE EMBODIMENTS

Figure 1:
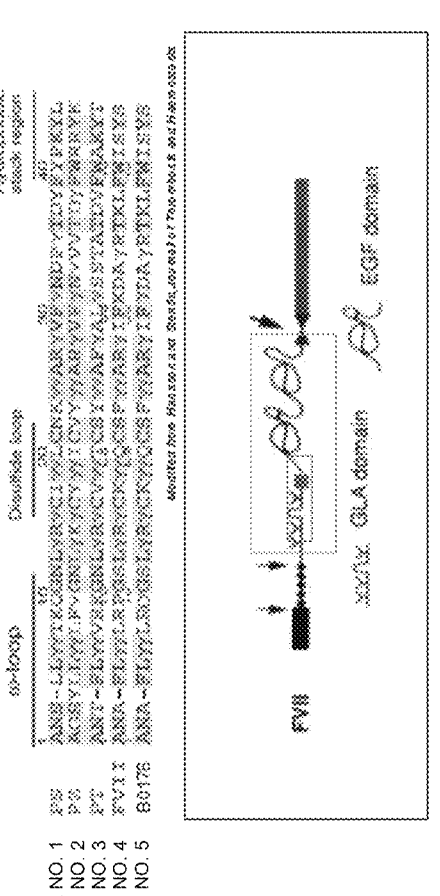
FIG. 1—Construction of a panel of Gla and Gla-EGF/Kringle domain proteins. Sequences shown from top to bottom are SEQ ID NOS: 1-5.

Like annexin, gamma-carboxyglutamic-acid (Gla)-domain proteins such as Factors II, VII, IX, X, protein C, and protein S bind anionic membranes. In fact, the Gla-domain has been used as a model for a small molecule that was rationally designed to be an apoptosis-specific probe (Cohen et al., 2009). Here, the inventors propose the utilization of the membrane targeting portions of these Gla-domain proteins as a novel class of biological probes specific for apoptosis and disease. The use of these naturally-occurring and targeted proteins may lead to enhanced specificity relative to current probes with the added advantage of a smaller size (<30 kDa). Even in larger embodiments, which would include EGF and/or Kringle domains, these proteins can still be smaller than Annexin V (37 kDa), and potentially as small as <5 kDa. These biologic probes can target PtdS cell-surface expression both in vitro and in vivo. Thus, it is possible to develop an apoptosis/disease targeting probe that is superior to Annexin V in affinity, specificity and size with the added potential for use as a therapeutic. These and other aspects of the disclosure are described in greater detail below.

Whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and are not limiting. For example, the term "including" shall mean "including, but not limited to." The word "about" means plus or minus 5% of the stated number.

An "isolated peptide or polypeptide," as used herein, is intended to refer to a peptide or polypeptide which is substantially free of other biological molecules, including peptides or polypeptides having distinct sequences. In some embodiments, the isolated peptide or polypeptide is at least about 75%, about 80%, about 90%, about 95%, about 97%, about 99%, about 99.9% or about 100% pure by dry weight. In some embodiments, purity can be measured by a method such as column chromatography, polyacrylamide gel electrophoresis, or HPLC analysis.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), (3-branched side chains (e.g., threonine, valine, isoleucine), and aromatic side chains (e.g., tyrosine, phenylalanine, tryptophan, histidine). Antibodies of the present disclosure can have one or more conservative amino acid substitutions yet retain antigen binding activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, in some embodiments about 90%, 91%, 92%, 93%, 94%, or 95%, in at least one embodiment at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. Comparison of sequences and determination of percent identity between two sequences can be accomplished using a mathematical algorithm, such as without limitation the AlignX™ module of VectorNTI™ (Invitrogen Corp., Carlsbad, CA). For AlignX™, the default parameters of multiple alignment are: gap opening penalty: 10; gap extension penalty: 0.05; gap separation penalty range: 8; % identity for alignment delay: 40. (further details at world-wide-web at invitrogen.com/site/us/en/home/LINNEA-Online-Guides/LINNEA-Communities/Vector-NTI-Community/Sequence-analysis-and-data-management-software-for-PCs/AlignX-Module-for-Vector-NTI-Advance.reg.us.html).

Another method for determining the best overall match between a query sequence (a sequence of the present disclosure) and a subject sequence, also referred to as a global sequence alignment, can be determined using the CLUSTALW computer program (Thompson et al., *Nucleic Acids Res,* 1994, 2(22): 4673-4680), which is based on the algorithm of Higgins et al., *Computer Applications in the Biosciences* (CABIOS), 1992, 8(2): 189-191). In a sequence alignment the query and subject sequences are both DNA sequences. The result of the global sequence alignment is in percent identity. Parameters that can be used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters can be used: Gap Opening Penalty=10, Gap Extension Parameter=0.05; Gap Separation Penalty Range=8; % Identity for Alignment Delay=40.

The nucleic acids can be present in whole cells, in a cell lysate, or in a partially purified or substantially pure form. A nucleic acid is "isolated" or "rendered substantially pure" when purified away from other cellular components with which it is normally associated in the natural environment.

To isolate a nucleic acid, standard techniques such as the following can be used: alkaline/SDS treatment, CsCl banding, column chromatography, agarose gel electrophoresis and others well known in the art.

I. PHOSPHATIDYLSERINE (PTDS)

A. Structure and Synthesis

Phosphatidylserine (abbreviated PtdS, Ptd-L-Ser or PS) is a phospholipid component, usually kept on the inner-leaflet (the cytosolic side) of cell membranes by an enzyme called flippase. When a cell undergoes apoptosis, phosphatidylserine is no longer restricted to the cytosolic part of the membrane, but becomes exposed on the surface of the cell. The chemical formula of PtdS is $C_{13}H_{24}NO_{10}P$ and has a molecular mass of 385.304. The structure is shown below:

Phosphatidylserine is biosynthesized in bacteria by condensing the amino acid serine with CDP (cytidine diphosphate)-activated phosphatidic acid. In mammals, phosphatidylserine is produced by base-exchange reactions with phosphatidylcholine and phosphatidylethanolamine. Conversely, phosphatidylserine can also give rise to phosphatidylethanolamine and phosphatidylcholine, although in animals the pathway to generate phosphatidylcholine from phosphatidylserine only operates in the liver.

B. Function

Early studies of phosphatidylserine distilled the chemical from bovine brain. Modern studies and commercially available products are made from soybeans, because of concerns about mad cow disease. The fatty acids attached to the serine in the soy product are not identical to those in the bovine product and is also impure. Preliminary studies in rats indicate that the soy product is at least as potent as that of bovine origin.

The U.S. FDA has given "qualified health claim" status to phosphatidylserine, stating that, "Consumption of phosphatidylserine may reduce the risk of dementia in the elderly" and "Consumption of phosphatidylserine may reduce the risk of cognitive dysfunction in the elderly."

Phosphatidylserine has been demonstrated to speed up recovery, prevent muscle soreness, improve well-being, and might possess ergogenic properties in athletes involved in cycling, weight training and endurance running. Soy-PtdS, in a dose dependent manner (400 mg), has been reported to be an effective supplement for combating exercise-induced stress by blunting the exercise-induced increase in cortisol levels. PtdS supplementation promotes a desirable hormonal balance for athletes and might attenuate the physiological deterioration that accompanies overtraining and/or overstretching. In recent studies, PtdS has been shown to enhance mood in a cohort of young people during mental stress and to improve accuracy during tee-off by increasing the stress resistance of golfers. First pilot studies indicate that PtdS supplementation might be beneficial for children with attention-deficit hyperactivity disorder.

Traditionally, PtdS supplements were derived from bovine cortex (BC-PS); however, due to the potential transfer of infectious diseases, soy-derived PS (S-PS) has been established as a potential safe alternative. Soy-derived PS is Generally Recognized As Safe (GRAS) and is a safe nutritional supplement for older persons if taken up to a dosage of 200 mg three times daily. Phosphatidylserine has been shown to reduce specific immune response in mice.

PtdS can be found in meat, but is most abundant in the brain and in innards such as liver and kidney. Only small amounts of PS can be found in dairy products or in vegetables, with the exception of white beans.

Annexin-A5 is a naturally-occurring protein with avid binding affinity for PtdS. Labeled-annexin-A5 enables visualization of cells in the early- to mid-apoptotic state in vitro or in vivo. Another PtdS binding protein is Mfge8. Technetium-labeled annexin-A5 enables distinction between malignant and benign tumors whose pathology includes a high rate of cell division and apoptosis in malignant compared with a low rate of apoptosis in benign tumors.

II. GLA DOMAIN PROTEINS

A. Gla Domains

The general structure for the Gla-domain proteins is that of a Gla domain followed by EGF domains and then a C terminal serine protease domain. The exceptions are prothrombin, which contains Kringle domains in place of EGF domains, and protein S, which does not have a serine protease domain but rather sex hormone-binding globulin-like (SHBG) domains (Hansson and Stenflo, 2005). The affinities of Gla-domain proteins to anionic membranes vary. Roughly, they fall into 3 categories 1) high affinity binders with a Kd of 30-50 nM, 2) mid-affinity binders with a $K_d$ of 100-200 nM and 3) low affinity binders with a Kd of 1000-2000 nM. The high affinity Gla domain proteins have been shown to bind anionic membranes with Protein S specifically demonstrating binding to apoptotic cells via its interaction with PtdS (Webb et al., 2002). The low affinity Gla domain proteins use a secondary receptor to bind to the cell membrane. For example, FVII utilizes Tissue Factor (TF). The Gla domain/$1^{st}$ EGF domain is believed to constitute the high affinity TF binding domain of FVII. Importantly for this approach, there are many studies that have shown TF up-regulation on the surface of cancer cells including colorectal cancer, NSCL carcinoma, and breast cancer and these high TF levels have been associated with a poor prognosis (Yu et al., 2004). Although the affinity for anionic membranes is relatively low for FVII, the addition of the high affinity TF interaction along with the documented up-regulation of TF in cancer makes it a potentially interesting cancer specific probe.

B. Gla Domain Containing Proteins

1. Factor II

Prothrombin, also known as coagulation factor II, is proteolytically cleaved to form thrombin in the coagulation cascade, which ultimately results in the stemming of blood loss. Thrombin in turn acts as a serine protease that converts soluble fibrinogen into insoluble strands of fibrin, as well as catalyzing many other coagulation-related reactions. It is primarily expressed in the liver.

The gene encoding prothrombin is located on chromosome 11 in the region of the centromere. It is composed of 14 exons and contains 24 kilobases of DNA. The gene encodes a signal region, a propeptide region, a glutamic acid domain, 2 Kringle regions, and a catalytic domain. The enzyme gamma-glutamyl carboxylase, in the presence of vitamin K, converts the N-terminal glutamic acid residues to gamma-carboxyglutamic acid residues. These gamma-carboxyglutamic acid residues are necessary for the binding of prothrombin to phospholipids on platelet membranes.

Inherited factor II deficiency is an autosomal recessive disorder that can manifest as hypoprothrombinemia, a decrease in the overall synthesis of prothrombin, or as dysprothrombinemia, the synthesis of dysfunctional prothrombin. Homozygous individuals are generally asymptomatic and have functional prothrombin levels of 2-25%. However, symptomatic individuals may experience easy bruising, epistaxis, soft-tissue hemorrhage, excessive post-operative bleeding, and/or menorrhagia.

Prothrombin plays a role in a role in chronic urticaria, an autoimmune disease, and various vascular disorders. Livedo vasculopathy is associated with immunoglobulin (Ig)M antiphosphatidylserine-prothrombin complex antibody. The presence of antiphosphatidylserine-prothrombin complex antibodies and histopathological necrotizing vasculitis in the upper-to-middle dermis indicates cutaneous leukocytoclastic angiitis rather than cutaneous polyarteritis nodosa.

Aside from the prothrombin deficiencies, another disorder of prothrombin is the prothrombin 20210a mutation. A familial cause of venous thromboembolism, the prothrombin 20210a mutation results in increased levels of plasma prothrombin and a concurrent increased risk for the development of thrombosis. Although the exact mechanism of this disorder has not been elucidated, the prothrombin 20210a mutation involves the substitution of an adenine for a guanine at position 20210 within the 3' untranslated region of the prothrombin gene. This mutation alters the polyadenylation site of the gene and results in increased mRNA synthesis, with a subsequent increase in protein expression.

2. Factor VII

Factor VII (formerly known as proconvertin) is one of the proteins that causes blood to clot in the coagulation cascade. The gene for factor VII is located on chromosome 13 (13q34). It is an enzyme of the serine protease class, and recombinant form of human factor VIIa (NovoSeven) has U.S. Food and Drug Administration approval for uncontrolled bleeding in hemophilia patients. It is sometimes used unlicensed in severe uncontrollable bleeding, although there have been safety concerns. A Biosimilar form of recombinant activated factor VII (AryoSeven) is manufactured by AryoGen Biopharma.

The main role of factor VII (FVII) is to initiate the process of coagulation in conjunction with tissue factor (TF/factor III). Tissue factor is found on the outside of blood vessels-normally not exposed to the bloodstream. Upon vessel injury, tissue factor is exposed to the blood and circulating factor VII. Once bound to TF, FVII is activated to FVIIa by different proteases, among which are thrombin (factor IIa), factor Xa, IXa, XIIa, and the FVIIa-TF complex itself. The most important substrates for FVIIa-TF are Factor X and Factor IX. Factor VII has been shown to interact with Tissue factor (TF).

The action of the factor is impeded by tissue factor pathway inhibitor (TFPI), which is released almost immediately after initiation of coagulation. Factor VII is vitamin K dependent; it is produced in the liver. Use of warfarin or similar anticoagulants decreases hepatic synthesis of FVII.

Deficiency is rare (congenital proconvertin deficiency) and inherits recessively. Factor VII deficiency presents as a hemophilia-like bleeding disorder. It is treated with recombinant factor VIIa (NovoSeven or AryoSeven). Recombinant factor VIIa is also used for people with hemophilia (with Factor VIII or IX deficiency) who have developed inhibitors against replacement coagulation factor. It has also been used in the setting of uncontrollable hemorrhage, but its role in this setting is controversial with insufficient evidence to support its use outside of clinical trials. The first report of its use in hemorrhage was in an Israeli soldier with uncontrollable bleeding in 1999. Risks of its use include an increase in arterial thrombosis.

3. Factor IX

Factor IX (or Christmas factor) is one of the serine proteases of the coagulation system; it belongs to peptidase family S1. The gene for factor IX is located on the X chromosome (Xq27.1-q27.2) and is therefore X-linked recessive: mutations in this gene affect males much more frequently than females. Deficiency of this protein causes hemophilia B. Factor IX is produced as a zymogen, an inactive precursor. It is processed to remove the signal peptide, glycosylated and then cleaved by factor XIa (of the contact pathway) or factor VIIa (of the tissue factor pathway) to produce a two-chain form where the chains are linked by a disulfide bridge. When activated into factor IXa, in the presence of Ca$^{2+}$, membrane phospholipids, and a Factor VIII cofactor, it hydrolyses one arginine-isoleucine bond in factor X to form factor Xa. Factor IX is inhibited by antithrombin.

Factors VII, IX, and X all play key roles in blood coagulation and also share a common domain architecture. The factor IX protein is composed of four protein domains. These are the Gla domain, two tandem copies of the EGF domain and a C-terminal trypsin-like peptidase domain which carries out the catalytic cleavage. The N-terminal EGF domain has been shown to at least in part be responsible for binding Tissue factor. Wilkinson et al. conclude that residues 88 to 109 of the second EGF domain mediate binding to platelets and assembly of the Factor X activating complex. The structures of all four domains have been solved. A structure of the two EGF domains and trypsin like domain was determined for the pig protein. The structure of the Gla domain, which is responsible for Ca(II)-dependent phospholipid binding, was also determined by NMR. Several structures of "super active" mutants have been solved which reveal the nature of Factor IX activation by other proteins in the clotting cascade.

Deficiency of factor IX causes Christmas disease (hemophilia B). Over 100 mutations of factor IX have been described; some cause no symptoms, but many lead to a significant bleeding disorder. Recombinant factor IX is used to treat Christmas disease, and is commercially available as BeneFIX. Some rare mutations of factor IX result in elevated clotting activity, and can result in clotting diseases, such as deep vein thrombosis.

4. Factor X

Factor X (Stuart-Prower factor; prothrombinase) is an enzyme of the coagulation cascade. The human factor X gene is located on the thirteenth chromosome (13q34). It is a serine endopeptidase (protease group S1). Factor X is synthesized in the liver and requires vitamin K for its synthesis. Factor X is activated into factor Xa by both factor IX (with its cofactor, factor VIII in a complex known as intrinsic Xase) and factor VII with its cofactor, tissue factor (a complex known as extrinsic Xase). The half life of factor X is 40-45 hours. It is therefore the first member of the final common pathway or thrombin pathway. It acts by cleaving prothrombin in two places (an arg-thr and then an arg-ile bond), which yields the active thrombin. This process is optimized when factor Xa is complexed with activated cofactor V in the prothrombinase complex. Factor X is part of fresh frozen plasma and the prothrombinase complex. The only commercially available concentrate is "Factor X P Behring" manufactured by CSL Behring.

Factor Xa is inactivated by protein Z-dependent protease inhibitor (ZPI), a serine protease inhibitor (serpin). The affinity of this protein for factor Xa is increased 1000-fold by the presence of protein Z, while it does not require protein Z for inactivation of factor XI. Defects in protein Z lead to increased factor Xa activity and a propensity for thrombosis.

Inborn deficiency of factor X is very rare (1:500,000), and may present with epistaxis (nosebleeds), hemarthrosis (bleeding into joints) and gastrointestinal blood loss. Apart from congenital deficiency, low factor X levels may occur occasionally in a number of disease states. For example, factor X deficiency may be seen in amyloidosis, where factor X is adsorbed to the amyloid fibrils in the vasculature. Also, deficiency of vitamin K or antagonism by warfarin (or similar medication) leads to the production of an inactive factor X. In warfarin therapy, this is desirable to prevent thrombosis. As of late 2007, four out of five emerging anti-coagulation therapeutics targeted this enzyme. Direct Xa inhibitors are popular anticoagulants.

Traditional models of coagulation developed in the 1960s envisaged two separate cascades, the extrinsic (tissue factor (TF)) pathway and the intrinsic pathway. These pathways converge to a common point, the formation of the Factor Xa/Va complex which together with calcium and bound on a phospholipids surface generate thrombin (Factor IIa) from prothrombin (Factor II). A new model, the cell-based model of anticoagulation appears to explain more fully the steps in coagulation. This model has three stages: 1) initiation of coagulation on TF-bearing cells, 2) amplification of the procoagulant signal by thrombin generated on the TF-bearing cell and 3) propagation of thrombin generation on the platelet surface. Factor Xa plays a key role in all three of these stages.

In stage 1, Factor VII binds to the transmembrane protein TF on the surface of cells and is converted to Factor VIIa. The result is a Factor VIIa/TF complex which catalyzes the activation of Factor X and Factor IX. Factor Xa formed on the surface of the TF-bearing cell interacts with Factor Va to form the prothrombinase complex which generates small amounts of thrombin on the surface of TF-bearing cells. In stage 2, the amplification stage, if enough thrombin has been generated, then activation of platelets and platelet associated cofactors occurs. In stage 3, thrombin generation, Factor XIa activates free Factor IX on the surface of activated platelets. The activated Factor IXa with Factor VIIIa forms the "tenase" complex. This complex activates more Factor X, which in turn forms new prothrombinase complexes with Factor Va. Factor Xa is the prime component of the pro-thrombinase complex which converts large amounts of prothrombin—the "thrombin burst." Each molecule of Factor Xa can generate 1000 molecules of thrombin. This large burst of thrombin is responsible for fibrin polymerization to form a thrombus.

Inhibition of the synthesis or activity of Factor X is the mechanism of action for many anticoagulants in use today. Warfarin, a synthetic derivative of coumarin, is the most widely used oral anticoagulant in the U.S. In some European countries, other coumarin derivatives (phenprocoumon and acenocoumarol) are used. These agents are vitamin K antagonists (VKA). Vitamin K is essential for the hepatic synthesis of Factors II (prothrombin), VII, IX and X. Heparin (unfractionated heparin) and its derivatives low molecular weight heparin (LMWH) bind to a plasma cofactor, antithrombin (AT) to inactivate several coagulation factors IIa, Xa, XIa and XIIa.

Recently a new series of specific, direct acting inhibitors of Factor Xa has been developed. These include the drugs rivaroxaban, apixaban, betrixaban, LY517717, darexaban (YM150), edoxaban and 813893. These agents have several theoretical advantages over current therapy. They may be given orally. They have rapid onset of action. And they may be more effective against Factor Xa in that they inhibit both free Factor Xa and Factor Xa in the prothrombinase complex.

5. Protein S

Protein S is a vitamin K-dependent plasma glycoprotein synthesized in the endothelium. In the circulation, Protein S exists in two forms: a free form and a complex form bound to complement protein C4b-binding protein (C4BP). In humans, Protein S is encoded by the PROS1 gene. The best characterized function of Protein S is its role in the anti coagulation pathway, where it functions as a cofactor to Protein C in the inactivation of Factors Va and VIIIa. Only the free form has cofactor activity.

Protein S can bind to negatively charged phospholipids via the carboxylated GLA domain. This property allows Protein S to function in the removal of cells which are undergoing apoptosis. Apoptosis is a form of cell death that is used by the body to remove unwanted or damaged cells from tissues. Cells which are apoptotic (i.e., in the process of apoptosis) no longer actively manage the distribution of phospholipids in their outer membrane and hence begin to display negatively charged phospholipids, such as phosphatidyl serine, on the cell surface. In healthy cells, an ATP (Adenosine triphosphate)-dependent enzyme removes these from the outer leaflet of the cell membrane. These negatively charged phospholipids are recognized by phagocytes such as macrophages. Protein S can bind to the negatively charged phospholipids and function as a bridging molecule between the apoptotic cell and the phagocyte. The bridging property of Protein S enhances the phagocytosis of the apoptotic cell, allowing it to be removed 'cleanly' without any symptoms of tissue damage such as inflammation occurring.

Mutations in the PROS1 gene can lead to Protein S deficiency which is a rare blood disorder which can lead to an increased risk of thrombosis. Protein S has been shown to interact with Factor V.

6. Protein C

Protein C, also known as autoprothrombin IIA and blood coagulation factor XIV, is a zymogenic (inactive) protein, the activated form of which plays an important role in regulating blood clotting, inflammation, cell death, and maintaining the permeability of blood vessel walls in humans and other animals. Activated protein C (APC) performs these operations primarily by proteolytically inactivating proteins Factor $V_a$ and Factor $VIII_a$. APC is classified as a serine protease as it contains a residue of serine in its active site. In humans, protein C is encoded by the PROC gene, which is found on chromosome 2.

The zymogenic form of protein C is a vitamin K-dependent glycoprotein that circulates in blood plasma. Its structure is that of a two-chain polypeptide consisting of a light chain and a heavy chain connected by a disulfide bond. The protein C zymogen is activated when it binds to thrombin, another protein heavily involved in coagulation, and protein C's activation is greatly promoted by the presence of thrombomodulin and endothelial protein C receptors (EPCRs). Because of EPCR's role, activated protein C is found primarily near endothelial cells (i.e., those that make up the walls of blood vessels), and it is these cells and leukocytes (white blood cells) that APC affects. Because of the crucial role that protein C plays as an anticoagulant, those with deficiencies in protein C, or some kind of resistance to APC, suffer from a significantly increased risk of forming dangerous blood clots (thrombosis).

Research into the clinical use of activated protein C also known as drotrecogin alfa-activated (branded Xigris) has been surrounded by controversy. The manufacturer Eli Lilly and Company ran an aggressive marketing campaign to promote its use in people with severe sepsis and septic shock including the sponsoring of the 2004 Surviving Sepsis Campaign Guidelines. A 2011 Cochrane review however found that its use cannot be recommended as it does not improve survival (and increases bleeding risk).

Human protein C is a vitamin K-dependent glycoprotein structurally similar to other vitamin K-dependent proteins affecting blood clotting, such as prothrombin, Factor VII, Factor IX and Factor X. Protein C synthesis occurs in the liver and begins with a single-chain precursor molecule: a 32 amino acid N-terminus signal peptide preceding a propeptide. Protein C is formed when a dipeptide of $Lys^{198}$ and $Arg^{199}$ is removed; this causes the transformation into a heterodimer with N-linked carbohydrates on each chain. The protein has one light chain (21 kDa) and one heavy chain (41 kDa) connected by a disulfide bond between $Cys^{183}$ and $Cys^{319}$.

Inactive protein C comprises 419 amino acids in multiple domains: one Gla domain (residues 43-88); a helical aromatic segment (89-96); two epidermal growth factor (EGF)-like domains (97-132 and 136-176); an activation peptide (200-211); and a trypsin-like serine protease domain (212-450). The light chain contains the Gla- and EGF-like domains and the aromatic segment. The heavy chain contains the protease domain and the activation petide. It is in this form that 85-90% of protein C circulates in the plasma as a zymogen, waiting to be activated. The remaining protein C zymogen comprises slightly modified forms of the protein. Activation of the enzyme occurs when a thrombin molecule cleaves away the activation peptide from the N-terminus of the heavy chain. The active site contains a catalytic triad typical of serine proteases ($His^{253}$, $Asp^{299}$ and $Ser^{402}$).

The activation of protein C is strongly promoted by thrombomodulin and endothelial protein C receptor (EPCR), the latter of which is found primarily on endothelial cells (cells on the inside of blood vessels). The presence of thrombomodulin accelerates activation by several orders of magnitude, and EPCR speeds up activation by a factor of 20. If either of these two proteins is absent in murine specimens, the mouse dies from excessive blood-clotting while still in an embryonic state. On the endothelium, APC performs a major role in regulating blood clotting, inflammation, and cell death (apoptosis). Because of the accelerating effect of thrombomodulin on the activation of protein C, the protein may be said to be activated not by thrombin but the thrombin-thrombomodulin (or even thrombin-thrombomodulin-EPCR) complex. Once in active form, APC may or may not remain bound to EPCR, to which it has approximately the same affinity as the protein zymogen.

The Gla domain is particularly useful for binding to negatively-charged phospholipids for anticoagulation and to EPCR for cytoprotection. One particular exosite augments protein C's ability to inactivate Factor $V_a$ efficiently. Another is necessary for interacting with thrombomodulin.

Protein C in zymogen form is present in normal adult human blood plasma at concentrations between 65-135 IU/dL. Activated protein C is found at levels approximately 2000 times lower than this. Mild protein C deficiency corresponds to plasma levels above 20 IU/dL, but below the normal range. Moderately severe deficiencies describe blood concentrations between 1 and 20 IU/dL; severe deficiencies yield levels of protein C that are below 1 IU/dL or are undetectable. Protein C levels in a healthy term infant average 40 IU/dL. The concentration of protein C increases until six months, when the mean level is 60 IU/dL; the level stays low through childhood until it reaches adult levels after adolescence. The half-life of activated protein C is around 15 minutes.

The protein C pathways are the specific chemical reactions that control the level of expression of APC and its activity in the body. Protein C is pleiotropic, with two main classes of functions: anticoagulation and cytoprotection (its direct effect on cells). Which function protein C performs depends on whether or not APC remains bound to EPCR after it is activated; the anticoagulative effects of APC occur when it does not. In this case, protein C functions as an anticoagulant by irreversibly proteolytically inactivating Factor $V_a$ and Factor $VIII_a$, turning them into Factor $V_i$ and Factor $VIII_i$ respectively. When still bound to EPCR, activated protein C performs its cytoprotective effects, acting on the effector substrate PAR-1, protease-activated receptor-1. To a degree, APC's anticoagulant properties are independent of its cytoprotective ones, in that expression of one pathway is not affected by the existence of the other.

The activity of protein C may be down-regulated by reducing the amount either of available thrombomodulin or of EPCR. This may be done by inflammatory cytokines, such as interleukin-1β (IL-1β) and tumor necrosis factor-α (TNF-α). Activated leukocytes release these inflammatory mediators during inflammation, inhibiting the creation of both thrombomodulin and EPCR, and inducing their shedding from the endothelial surface. Both of these actions down-regulate protein C activation. Thrombin itself may also have an effect on the levels of EPCR. In addition, proteins released from cells can impede protein C activation, for example eosinophil, which may explain thrombosis in hypereosinophilic heart disease. Protein C may be up-regulated by platelet factor 4. This cytokine is conjectured to improve activation of protein C by forming an electrostatic bridge from protein C's Gla domain to the glycosaminoglycan (GAG) domain of thrombomodulin, reducing the Michaelis constant ($K_M$) for their reaction. In addition, Protein C is inhibited by protein C inhibitor.

A genetic protein C deficiency, in its mild form associated with simple heterozygosity, causes a significantly increased risk of venous thrombosis in adults. If a fetus is homozygous or compound heterozygous for the deficiency, there may be a presentation of purpura fulminans, severe disseminated intravascular coagulation and simultaneous venous thromboembolism in the womb; this is very severe and usually fatal. Deletion of the protein C gene in mice causes fetal death around the time of birth. Fetal mice with no protein C develop normally at first, but experience severe bleeding, coagulopathy, deposition of fibrin and necrosis of the liver. The frequency of protein C deficiency among asymptomatic individuals is between 1 in 200 and 1 in 500. In contrast, significant symptoms of the deficiency are detectable in 1 in 20,000 individuals. No racial nor ethnic biases have been detected.

Activated protein C resistance occurs when APC is unable to perform its functions. This disease has similar symptoms to protein C deficiency. The most common mutation leading to activated protein C resistance among Caucasians is at the cleavage site in Factor V for APC. There, $Arg^{506}$ is replaced with Gln, producing Factor V Leiden. This mutation is also called a R506Q. The mutation leading to the loss of this cleavage site actually stops APC from effectively inactivating both Factor Va and Factor Villa. Thus, the person's blood clots too readily, and he is perpetually at an increased risk for thrombosis. Individuals heterozygous for the Factor $V_{Leiden}$ mutation carry a risk of venous thrombosis 5-7 times higher than in the general population. Homozygous subjects have a risk 80 times higher. This mutation is also the most common hereditary risk for venous thrombosis among Caucasians.

Around 5% of APC resistance is not associated with the above mutation and Factor $V_{Leiden}$. Other genetic mutations cause APC resistance, but none to the extent that Factor $V_{Leiden}$ does. These mutations include various other versions of Factor V, spontaneous generation of autoantibodies targeting Factor V, and dysfunction of any of APC's cofactors. Also, some acquired conditions may reduce the efficacy of APC in performing its anticoagulative functions. Studies suggest that between 20% and 60% of thrombophilic patients suffer from some form of APC resistance.

C. Gla Domain Peptides and Polypeptide

The present disclosure contemplates the design, production and use of various Gla domain-containing peptides and polypeptides. The structural features of these molecules are as follows. First, the peptides or polypeptides have a Gla domain containing about 30-45 consecutive residues comprising a Gla domain. Thus, the term "a peptide having no more than "X" consecutive residues," even when including the term "comprising," cannot be understood to comprise a greater number of consecutive residues. Second, the peptides and polypeptides may contain additional non-Gla domain residues, such as EGF domains, Kringle domains, Fc domains, etc.

In general, the peptides and polypeptides will be 300 residues or less, again, comprising 30-45 consecutive residues of Gla domain. The overall length may be 30, 40, 50, 60, 70, 80, 90, 100, 125, 150, 175, 200, 225, 250, 275 and up to 300 residues. Ranges of peptide length of 50-300 residues, 100-300 residues, 150-300 residues 200-300, residues, 50-200 residues, 100-200 residues, and 150-300 residues, and 150-200 residues are contemplated. The number of consecutive Gla residues may be 3, 4, 5, 6, 7, 8, 9, 10, 11, 12, 13, 14 or 15.

The present disclosure may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

D. Synthesis

It will be advantageous to produce peptides and polypeptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry (1973). These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides and polypeptides of the disclosure are preferably devoid of benzylated or methylbenzylated amino acids. Such protecting group moieties may be used in the course of synthesis, but they are removed before the peptides and polypeptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

E. Linkers

Linkers or cross-linking agents may be used to fuse Gla domain peptides or polypeptides to other proteinaceous sequences (e.g., antibody Fc domains). Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Hetero-bifunctional reagents contain two different functional groups. By taking advantage of the differential reactivities of the two different functional groups, cross-linking can be controlled both selectively and sequentially. The bifunc-tional cross-linking reagents can be divided according to the specificity of their functional groups, e.g., amino-, sulfhy-dryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorpo-rated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

F. Additional Peptide/Polypeptide Sequences

One factor drug development is to achieve adequate circulating half-lives, which impact dosing, drug adminis-tration and efficacy, and this has particular important to biotherapeutics. Small proteins below 60 kD are cleared rapidly by the kidney and therefore do not reach their target. This means that high doses are needed to reach efficacy. The modifications currently used to increase the half-life of proteins in circulation include: PEGylation; conjugation or genetic fusion with proteins, e.g., transferrin (WO06096515A2), albumin, growth hormone (U.S. Patent Publication 2003104578AA); conjugation with cellulose (Levy and Shoseyov, 2002); conjugation or fusion with Fc fragments; glycosylation and mutagenesis approaches (Carter, 2006).

In the case of PEGylation, polyethylene glycol (PEG) is conjugated to the protein, which can be for example a plasma protein, antibody or antibody fragment. The first studies regarding the effect of PEGylation of antibodies were performed in the 1980s. The conjugation can be done either enzymatically or chemically and is well established in the art (Chapman, 2002; Veronese and Pasut, 2005). With PEGylation the total size can be increased, which reduces the chance of renal filtration. PEGylation further protects from proteolytic degradation and slows the clearance from the blood. Further, it has been reported that PEGylation can reduce immunogenicity and increase solubility. The improved pharmacokinetics by the addition of PEG is due to several different mechanisms: increase in size of the mol-ecule, protection from proteolysis, reduced antigenicity, and the masking of specific sequences from cellular receptors. In the case of antibody fragments (Fab), a 20-fold increase in plasma half-life has been achieved by PEGylation (Chap-man, 2002).

To date there are several approved PEGylated drugs, e.g., PEG-interferon alpha2b (PEG-INTRON) marketed in 2000 and alpha2a (Pegasys) marketed in 2002. A PEGylated antibody fragment against TNF alpha, called Cimzia or Certolizumab Pegol, was filed for FDA approval for the treatment of Crohn's disease in 2007 and has been approved on Apr. 22, 2008. A limitation of PEGylation is the difficulty in synthesizing long monodisperse species, especially when PEG chains over 1000 kD are needed. For many applica-tions, polydisperse PEG with a chain length over 10000 kD is used, resulting in a population of conjugates having different length PEG chains, which need extensive analytics to ensure equivalent batches between productions. The dif-ferent length of the PEG chains may result in different biological activities and therefore different pharmacokinet-ics. Another limitation of PEGylation is a decrease in affinity or activity as it has been observed with alpha-interferon Pegasys, which has only 7% of the antiviral activity of the native protein, but has improved pharmacokinetics due to the enhanced plasma half-life.

Another approach is to conjugate the drug with a long lived protein, e.g., albumin, which is 67 kD and has plasma half-life of 19 days in human. Albumin is the most abundant protein in plasma and is involved in plasma pH regulation, but also serves as a carrier of substances in plasma. In the case of CD4, increased plasma half-life has been achieved after fusing it to human serum albumin (Yeh et al., 1992). Other examples for fusion proteins are insulin, human growth hormone, transferrin and cytokines (Duttaroy et al., 2005; Melder et al., 2005; Osborn et al., 2002a; Osborn et al., 2002b; Sung et al., 2003) and see (U.S. Patent Publica-tion 2003104578A1, WO06096515A2, and WO07047504A2, herein incorporated in entirety by refer-ence).

The effect of glycosylation on plasma half-life and protein activity has also been extensively studied. In the case of tissue plasminogen activator (tPA), the addition of new glycosylation sites decreased the plasma clearance, and improved the potency (Keyt et al., 1994). Glycoengineering has been successfully applied for a number of recombinant proteins and immunoglobulins (Elliott et al., 2003; Raju and Scallon, 2007; Sinclair and Elliott, 2005; Umana et al., 1999). Further, glycosylation influences the stability of immunoglobulins (Mimura et al., 2000; Raju and Scallon, 2006).

Another molecule used for fusion proteins is the Fc fragment of an IgG (Ashkenazi and Chamow, 1997). The Fc fusion approach has been utilized, for example in the Trap Technology developed by Regeneron (e.g., IL1 trap and VEGF trap). The use of albumin to extend the half-life of peptides has been described in U.S. Patent Publication 2004001827A1. Positive effects of albumin have also been reported for Fab fragments and scFv-HSA fusion protein. It has been demonstrated that the prolonged serum half-life of albumin is due to a recycling process mediated by the FcRn (Anderson et al., 2006; Chaudhury et al., 2003).

Another strategy is to use directed mutagenesis tech-niques targeting the interaction of immunoglobulins to their receptor to improve binding properties, i.e., affinity matu-ration in the Fc region. With an increased affinity to FcRn a prolonged half-life can be achieved in vivo (Ghetie et al., 1997; Hinton et al., 2006; Jain et al., 2007; Petkova et al., 2006a; Vaccaro et al., 2005). However, affinity maturation strategies require several rounds of mutagenesis and testing. This takes time, is costly and is limited by the number of amino acids that when mutated result in prolonged half-lives. Therefore, simple alternative approaches are needed to improve the in vivo half-life of biotherapeutics. Therapeu-tics with extended half-lives in vivo are especially important for the treatment of chronic diseases, autoimmune disorders, inflammatory, metabolic, infectious, and eye diseases, and cancer, especially when therapy is required over a long time period. Accordingly, a need still exists for the development of therapeutic agents (e.g., antibodies and Fc fusion proteins) with enhanced persistence and half-lives in circulation, in order to reduce the dosage and/or the frequency of injections of a variety of therapeutic agents.

G. Labels

The peptides and polypeptides of the present disclosure may be conjugated to labels for diagnostic purposes. A label in accordance with the present disclosure is defined as any moiety which may be detected using an assay. Non-limiting examples of reporter molecules include enzymes, radiolabels, haptens, fluorescent labels, phosphorescent molecules, chemiluminescent molecules, chromophores, photoaffinity molecules, colored particles or ligands, such as biotin.

Label conjugates are generally preferred for use as diagnostic agents. Diagnostic agents generally fall within two classes, those for use in in vitro diagnostics, and those for use in vivo diagnostic protocols, generally known as "directed imaging." Many appropriate imaging agents are known in the art, as are methods for their attachment to peptides and polypeptides (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled peptides and polypeptides may be produced according to well-known methods in the art. For instance, peptides and polypeptides can be iodinated by contact with sodium and/or potassium iodide and a chemical oxidizing agent such as sodium hypochlorite, or an enzymatic oxidizing agent, such as lactoperoxidase. Peptides may be labeled with technicium$^{99m}$ by ligand exchange process, for example, by reducing pertechnate with stannous solution, chelating the reduced technetium onto a Sephadex column and applying the peptide to this column. Alternatively, direct labeling techniques may be used, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptide are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of conjugate contemplated is that intended primarily for use in vitro, where the peptide is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and is described, for example, in U.S. Pat. Nos. 3,817,837, 3,850,752, 3,939,350, 3,996,345, 4,277,437, 4,275,149 and 4,366,241.

Other methods are known in the art for the attachment or conjugation of a peptide to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Peptides or polypeptides may also be reacted with an enzyme in the presence of a coupling agent such as glutaraldehyde or periodate. Conjugates with fluorescein markers are prepared in the presence of these coupling agents or by reaction with an isothiocyanate.

IV. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the peptides and polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Disease States and Conditions

1. Cancer

Background. Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia. There are hundreds of different forms of human cancers, and with an increasing understanding of the underlying genetics and biology of cancer, these forms are being further subdivided and reclassified.

Determining what causes cancer is complex. Many things are known to increase the risk of cancer, including tobacco use, certain infections, radiation, lack of physical activity, obesity, and environmental pollutants. These can directly damage genes or combine with existing genetic faults within cells to cause the disease. Approximately five to ten percent of cancers are entirely hereditary.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million). Rates are rising as more people live to an old age and as mass lifestyle changes occur in the developing world.

Treatments fall in to five general categories: surgery, chemotherapy, radiation, alternative medicine and palliative care. Surgery is the primary method of treatment of most isolated solid cancers and may play a role in palliation and prolongation of survival. It is typically an important part of making the definitive diagnosis and staging the tumor as biopsies are usually required. In localized cancer surgery typically attempts to remove the entire mass along with, in certain cases, the lymph nodes in the area. For some types of cancer this is all that is needed to eliminate the cancer.

Chemotherapy in addition to surgery has proven useful in a number of different cancer types including: breast cancer, colorectal cancer, pancreatic cancer, osteogenic sarcoma, testicular cancer, ovarian cancer, and certain lung cancers. The effectiveness of chemotherapy is often limited by toxicity to other tissues in the body.

Radiation therapy involves the use of ionizing radiation in an attempt to either cure or improve the symptoms of cancer. It is used in about half of all cases and the radiation can be from either internal sources in the form of brachytherapy or external sources. Radiation is typically used in addition to surgery and or chemotherapy but for certain types of cancer such as early head and neck cancer may be used alone. For painful bone metastasis it has been found to be effective in about 70% of people.

Alternative and complementary treatments include a diverse group of health care systems, practices, and products that are not part of conventional medicine "Complementary medicine" refers to methods and substances used along with conventional medicine, while "alternative medicine" refers to compounds used instead of conventional medicine. Most complementary and alternative medicines for cancer have not been rigorously studied or tested. Some alternative treatments have been investigated and shown to be ineffective but still continue to be marketed and promoted.

Finally, palliative care refers to treatment which attempts to make the patient feel better and may or may not be combined with an attempt to attack the cancer. Palliative care includes action to reduce the physical, emotional, spiritual, and psycho-social distress experienced by people with cancer. Unlike treatment that is aimed at directly killing cancer cells, the primary goal of palliative care is to improve the patient's quality of life.

Gla domain activity. In the context of the present disclosure, it is contemplated that the engineered Gla proteins may be used as anti-cancer agents in several different fashions. First, cancer patients often suffer from a hypercoagulable state which can lead to embolism and death. In this embodiment, the Gla domain proteins (optionally linked to an Fc region) are administered into the vasculature of the subject in amounts sufficient to reduce emboli formation and pathological coagulation. Such Gla domain proteins disclosed herein are useful in reducing, blocking and/or inhibiting pathologic coagulation in such patients.

Also, it is known that PtdS plays a role in suppressing the immune response to cancer. Thus, in another embodiment, the inventors envision the use of Gla domain proteins to bind and block/mask PtdS on cancer cells. This serves to prevent tolerogenic signaling through PtdS that induces anti-inflammatory cytokines and suppresses pro-inflammatory cytokines, thereby facilitating immune escape of the cancer cells. This may prove a particularly useful approach when combined with other "standard" cancer therapeutics, as discussed in detail below.

2. Autoimmune/Inflammatory Disease

Background. The present disclosure contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, systemic lupus erythematosus, psoriasis, vasculitis, Wegener's granulomatosis, Addison's disease, alopecia, antiphospholipid syndrome, Behcet's disease, celiac disease, chronic fatigue syndrome, ulcerative colitis, type I diabetes, fibromyalgia, autoimmune gastritis, Goodpasture syndrome, Graves' disease, idiopathic thrombocytopenic purpura (ITP), myasthenia gravis, pemphigus vulgaris, primary biliary cirrhosis, rheumatic fever, sarcoidosis, scleroderma, vitiligo, vasculitis, small vessel vasculitis, hepatitis, primary biliary cirrhosis, sarcoidosis, scleroderma, graft versus host disease (acute and chronic), aplastic anemia, or cyclic neutropenia. The diagnosis and treatment of these diseases are well documented in the literature.

Gla domain activity. It is known that certain immune disorders are characterized by deficient phagocytosis of apoptotic cells, leading to secondary necrosis, pro-inflammatory signaling and autoantibody production. Further, plasma membrane-derived vesicles (PMVs) containing PtdS on their surface are shed from apoptotic cells and are thought to bind to immune cells, such as macrophages (DeRose et al., 2011). Gla domain proteins can be used to mask the PtdS found on the surface of PMVs, thereby reducing the "decoy" effect of the PMVs and permitting phagocytosis of apoptotic cells. This should break the cycle of continued inflammatory signaling and reduce immune hyperactivation.

3. Hypercoagulation Disorders

Background. Hypercoagulation disorders give rise to an increased tendency for clotting of the blood, which put a patient at risk for obstruction of veins and arteries. In normal hemostasis, or the stoppage of bleeding, clots form at the site of the blood vessel's injury. In hypercoagulation, clots develop in circulating blood. When this occurs throughout the body's blood vessels, a condition known as thrombosis can arise. Thrombosis can lead to infarction, or death of tissue. Hypercoagulation disorders include hyperhomocystinemia, antithrombin III deficiency, factor V leyden, and protein C or protein S deficiency.

The diagnosis of hypercoagulation disorders is completed with a combination of physical examination, medical history, and blood tests. When found, coumadin and heparin anticoagulants may be administered to reduce the clotting effects and maintain fluidity in the blood. The prognosis for patients with hypercoagulation disorders varies depending on the severity of the clotting and thrombosis, but if unde-tected and untreated, thrombosis could lead to pulmonary embolism and death.

Sickle cell disease (SCD), though not a clotting disorder, has some of the same manifestations. Interestingly, an increased level of surface expressed PtdS on a subpopulation of erythrocytes is a universal feature of this disease (Wood et al., *Blood*, Vol 88, No 5 (September 1), 1996). SCD is an autosomal recessive genetic blood disorder with overdomi-nance, characterized by red blood cells that assume an abnormal, rigid, sickle shape. Sickling decreases the cells' flexibility and results in a risk of various complications. The sickling occurs because of a mutation in the hemoglobin gene. Life expectancy is shortened. Sickle-cell disease occurs more commonly in people (or their descendants) from parts of tropical and sub-tropical sub-Saharan regions where malaria is or was common. In areas where malaria is common, there is a fitness benefit in carrying only a single sickle-cell gene (sickle cell trait). Those with only one of the two alleles of the sickle-cell disease, while not totally resistant, are more tolerant to the infection and thus show less severe symptoms when infected.

Sickle-cell anaemia is the name of a specific form of sickle-cell disease in which there is homozygosity for the mutation that causes HbS. Sickle-cell anaemia is also referred to as "HbSS," "SS disease," "hemoglobin S" or permutations thereof. In heterozygous people, who have only one sickle gene and one normal adult haemoglobin gene, it is referred to as "HbAS" or "sickle cell trait." Other, rarer forms of sickle-cell disease include sickle-hemoglobin C disease (HbSC), sickle beta-plus-thalassemia (HbS/$\beta^+$) and sickle beta-zero-thalassaemia (HbS/$\beta^0$). These other forms of sickle-cell disease are compound heterozygous states in which the person has only one copy of the mutation that causes HbS and one copy of another abnormal hemo-globin allele.

In particular aspects, SCD can relate to blood flow. The vaso-occlusive crisis is caused by sickle-shaped red blood cells that obstruct capillaries and restrict blood flow to an organ, resulting in ischemia, pain, necrosis and often organ damage. The frequency, severity, and duration of these crises vary considerably. Painful crises are treated with hydration, analgesics, and blood transfusion; pain management requires opioid administration at regular intervals until the crisis has settled. For milder crises, a subgroup of patients manages on NSAIDs (such as diclofenac or naproxen). For more severe crises, most patients require inpatient manage-ment for intravenous opioids; patient-controlled analgesia (PCA) devices are commonly used in this setting. Vaso-occlusive crisis involving organs such as the penis or lungs are considered an emergency and treated with red-blood cell transfusions. Diphenhydramine is sometimes effective for the itching associated with the opioid use. Incentive spirom-etry, a technique to encourage deep breathing to minimize the development of atelectasis, is recommended.

Gla domain activity. The present invention contemplates the use of Gla domains to control or modulate the pro-coagulant actions of PtdS in hypercoagulation. PtdS surface expression is a potent stimulator of the coagulation cascade. Masking exposed PtdS via the use of Gla domain polypep-tides could inhibit or dampen this cascade. This treatment could be particularly beneficial for SCA individuals where it is believed that only a small population of RBCs may be responsible for the hypercoagulability associated with the disease 4. Viral Infection Background. A virus is a small infectious agent that can replicate only inside the living cells of an organism. Viruses can infect all types of organisms, from animals and plants to bacteria and archaea. About 5,000 viruses have been described in detail, although there are millions of different types. Viruses are found in almost every ecosystem on Earth and are the most abundant type of biological entity.

Virus particles (known as virions) consist of two or three parts: i) the genetic material made from either DNA or RNA, long molecules that carry genetic information; ii) a protein coat that protects these genes; and in some cases iii) an envelope of lipids that surrounds the protein coat when they are outside a cell. The shapes of viruses range from simple helical and icosahedral forms to more complex structures. The average virus is about one one-hundredth the size of the average bacterium. Most viruses are too small to be seen directly with an optical microscope.

Viruses spread in many ways; viruses in plants are often transmitted from plant to plant by insects that feed on plant sap, such as aphids; viruses in animals can be carried by blood-sucking insects. These disease-bearing organisms are known as vectors. Influenza viruses are spread by coughing and sneezing. Norovirus and rotavirus, common causes of viral gastroenteritis, are transmitted by the fecal-oral route and are passed from person to person by contact, entering the body in food or water. HIV is one of several viruses transmitted through sexual contact and by exposure to infected blood. The range of host cells that a virus can infect is called its "host range." This can be narrow or, as when a virus is capable of infecting many species, broad.

Viral infections in animals provoke an immune response that usually eliminates the infecting virus. Immune responses can also be produced by vaccines, which confer an artificially acquired immunity to the specific viral infection. However, some viruses including those that cause AIDS and viral hepatitis evade these immune responses and result in chronic infections. Antibiotics have no effect on viruses, but several antiviral drugs have been developed.

A variety of diseases are fostered by virus infections, including influenza, human immunodeficiency virus, dengue virus, West Nile virus, smallpox virus, respiratory syncytial virus, Korean hemorrhagic fever virus, chickenpox, vari-cella zoster virus, herpes simplex virus 1 or 2, Epstein-Barr virus, Marburg virus, hantavirus, yellow fever virus, hepa-titis A, B, C or E, Ebola virus, human papilloma virus, rhinovirus, Coxsackie virus, polio virus, measles virus, rubella virus, rabies virus, Newcastle disease virus, rotavi-rus, HTLV-1 and -2.

Gla domain activity. PtdS is segregated to the inner leaflet of the plasma membrane of resting mammalian cells. Loss of phosphatidylserine asymmetry occurs during apoptosis, cell injury and cell activation such as observed during viral infection. This results from inhibition of the translocases or activation of phosphatidylserine exporters, or lipid-scram-bling enzymes, such as scramblases (Soares et al., 2008). Viruses activate host cells to replicate efficiently, and virus-induced cell activation may lead to rises in intracellular Ca$^{2+}$ that, in turn, cause phosphatidylserine externalization by activating phosphatidylserine exporters and by inhibiting phosphatidylserine import by translocases. Moreover, phos-phatidylserine translocation to the external host cell surface could be an early event associated with virus-induced apop-tosis (Soares et al., 2008).

PtdS on the surface of infected cells, budding virions or microvesicles derived from pre-apoptotic cells leads to immune evasion. Using the Gla domain polypeptides of the present disclosure to mask the PtdS on these membranes, normal immune function can more effectively address the viral challenge, thus reducing viral load, limiting infection, and destroying virions and infected cells.

5. Sepsis

Background. In sepsis, inflammation and thrombosis are both cause and result of interactions between circulating (for example, leukocytes and platelets), endothelial and smooth muscle cells. Microparticles are pro-inflammatory and pro-coagulant fragments originating from plasma membrane generated after cellular activation and released in body fluids. In the vessel, they constitute a pool of bioactive effectors pulled from diverse cellular origins and may act as intercellular messengers. Microparticles expose phosphatidylserine, a procoagulant phospholipid made accessible after membrane remodeling, and tissue factor (TF), the initiator of blood coagulation at the endothelial and leukocyte surface. They constitute a secretion pathway for IL-1β and upregulate the pro-inflammatory response of target cells. Microparticles circulate at low levels in healthy individuals, but undergo phenotypic and quantitative changes that could play a pathophysiological role in inflammatory diseases. Microparticles (MPs) may participate in the pathogenesis of sepsis through multiple ways. They are able to regulate vascular tone and are potent vascular pro-inflammatory and pro-coagulant mediators. Microparticles' abilities are of increasing interest in deciphering the mechanisms underlying the multiple organ dysfunction of septic shock.

The plasma membrane of endothelial cells and monocytes is reorganized with externalisation of phosphatidylserine and encrypted tissue factor TF expression, allowing factor VII (FVIIa) activation and thrombin (FIIa) generation at the cell surface. Blebbing occurs, with release of microparticles bearing TF, resulting in an increased surface for procoagulant reactions. Platelet adhesion and aggregation also occur with the release of MPs; platelets and MPs bear GPIba, a cofactor for factor XI activation by thrombin, leading to the propagation phase with high levels of thrombin generation and fibrin formation. Endothelial TF-bearing MPs allow transfer of TF to PMNs, increasing TF dissemination and thrombotic microangiopathy or disseminated intravascular coagulopathy. TF initiation of blood coagulation is quickly down-regulated by tissue factor pathway inhibitor (TFPI) on endothelial and monocytic cell surfaces, as on MPs. Endothelial protein C receptor (EPCR)-bound protein C is activated by the thrombin-thrombomodulin complex and activated protein C (APC) inhibits factor Va and factor VIIIa, limiting the propagation phase of thrombin generation. EPCR-bound APC also regulates NF-ΚB, with cytoprotective effects on endothelial cells and monocytes. APC induces blebbing, with emission of EPCR-bearing MPs able to activate protein C, resulting in the dissemination of anticoagulant and antiapoptotic activities.

Gla domain activity. The present invention contemplates the use of Gla domains to control or modulate the pro-coagulant actions of microparticles containing PtdS and TF on their surface. They can also down-regulate the related pro-inflammatory signaling that occurs in sepsis, for example, through IL-1β, as well as modulating the effects of PtdS-bearing microparticles on vascular tone.

C. Treatment Methods

Peptides and polypeptides can be administered to mammalian subjects (e.g., human patients) alone or in conjunction with other drugs that treat the diseases set forth above. The dosage required depends on the choice of the route of administration; the nature of the formulation, including additional agents attached to the polypeptide; the nature of the patient's illness; the subject's size, weight, surface area, age, and sex; further combination therapies; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Combination Therapies

It is common in many fields of medicine to treat a disease with multiple therapeutic modalities, often called "combination therapies." To treat disorders using the methods and compositions of the present disclosure, one would generally contact a target cell or subject with a Gla domain polypeptide and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the Gla domain polypeptide and the other includes the other agent.

Alternatively, the Gla domain polypeptide may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the Gla domain protein or the other therapy/agent will be desired. Various combinations may be employed, where the Gla domain protein is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated.

Agents or factors suitable for use in a combined therapy against a cancer include radionuclides, chemotherapeutic agents or toxins. Specific chemotherapeutics include temozolomide, epothilones, melphalan, carmustine, busulfan, lomustine, cyclophosphamide, dacarbazine, polifeprosan, ifosfamide, chlorambucil, mechlorethamine, busulfan, cyclophosphamide, carboplatin, cisplatin, thiotepa, capecitabine, streptozocin, bicalutamide, flutamide, nilutamide, leuprolide acetate, doxorubicin hydrochloride, bleomycin sulfate, daunorubicin hydrochloride, dactinomycin, liposomal daunorubicin citrate, liposomal doxorubicin hydro-chloride, epirubicin hydrochloride, idarubicin hydrochlo-ride, mitomycin, doxorubicin, valrubicin, anastrozole, toremifene citrate, cytarabine, fluorouracil, fludarabine, floxuridine, interferon α-2b, plicamycin, mercaptopurine, methotrexate, interferon α-2a, medroxyprogersterone acetate, estramustine phosphate sodium, estradiol, leupro-lide acetate, megestrol acetate, octreotide acetate, deithyl-stilbestrol diphosphate, testolactone, goserelin acetate, etoposide phosphate, vincristine sulfate, etoposide, vinblas-tine, etoposide, vincristine sulfate, teniposide, trastuzumab, gemtuzumab ozogamicin, rituximab, exemestane, irinotecan hydrocholride, asparaginase, gemcitabine hydrochloride, altretamine, topotecan hydrochloride, hydroxyurea, cladrib-ine, mitotane, procarbazine hydrochloride, vinorelbine tar-trate, pentrostatin sodium, mitoxantrone, pegaspargase, denileukin diftitix, altretinoin, porfimer, bexarotene, pacli-taxel, docetaxel, arsenic trioxide, or tretinoin. Toxins include *Pseudomonas* exotoxin (PE38), ricin A chain, diphtheria toxin, Besides PE and RT, Pokeweed antiviral protein (PAP), saporin and gelonin. Radionuclides for cancer therapy include Y-90, P-32, I-131, In-111, Sr-89, Re-186, Sm-153, and Sn-117m.

Agents or factors suitable for use in a combined therapy against an autoimmune disorder include anti-inflammatories and immune-modulating compositions. These include pred-nisone, methylpredni sone, Venipred, Celestone, hydrocor-tisone, triamcinoclone, Aristonpan Intra-Articular injection, Methapred, Rayos oral, betamethasone, and etanercept.

Agents or factors suitable for use in a combined therapy against cardiovascular disease include beta blockers, anti-hypertensives, cardiotonics, anti-thrombotics, vasodilators, hormone antagonists, endothelin antagonists, cytokine inhibitors/blockers, calcium channel blockers, phosphodies-terase inhibitors and angiotensin type 2 antagonists.

Agents or factors suitable for use in a combined therapy against a hypercoagulation disorder include anti-coagulants such as heparin and warfarin.

Agents or factors suitable for use in a combined therapy against a viral infections include Abacavir, Aciclovir, Acy-clovir, Adefovir, Amantadine, Amprenavir, Ampligen, Arbi-dol, Atazanavir, Atripla, Boceprevirertet, Cidofovir, Com-bivir, Darunavir, Delavirdine, Didanosine, Docosanol, Edoxudine, Efavirenz, Emtricitabine, Enfuvirtide, Ente-cavir, Entry inhibitors, Famciclovir, Fomivirsen, Fosampre-navir, Foscarnet, Fosfonet, Ganciclovir, Ibacitabine, Imuno-vir, Idoxuridine, Imiquimod, Indinavir, Inosine, Integrase inhibitor, Interferon type III, Interferon type II, Interferon type I, Interferon, Lamivudine, Lopinavir, Loviride, Mara-viroc, Moroxydine, Methisazone, Nelfinavir, Nevirapine, Nexavir, Nucleoside analogues, Oseltamivir, Peginterferon alfa-2a, Penciclovir, Peramivir, Pleconaril, Podophyllotoxin, Protease inhibitor, Raltegravir, Reverse transcriptase inhibi-tor, Ribavirin, Rimantadine, Ritonavir, Pyramidine, Saqui-navir, Stavudine, Synergistic enhancer (antiretroviral), Tea tree oil, Telaprevir, Tenofovir, Tenofovir disoproxil, Tipra-navir, Trifluridine, Trizivir, Tromantadine, Truvada, Valaci-clovir, Valganciclovir, Vicriviroc, Vidarabine, Viramidine, Zalcitabine, Zanamivir and Zidovudine.

The skilled artisan is directed to "Remington's Pharma-ceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treatment.

V. EXAMPLES

The following examples are included to demonstrate preferred embodiments of the disclosure. It should be appre-ciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

The affinities of Gla-domain proteins for cell membranes have been determined in vitro by using prepared phospho-lipid vesicles (Shah et al., 1998; Nelsestuen, 1999). How these in vitro values translate to an in vivo context, however, has not been fully elucidated. The interaction of FVII with TF, for example, underscores the fact that although the Gla domains of these proteins are very homologous, additional differences in their cell membrane binding specificity and affinity may be mediated through their EGF and/or Kringle domains. Unfortunately, these interactions cannot be reca-pitulated by studies based solely on phospholipid vesicles and may remain unidentified.

Therefore, inventors proposed making and testing the Gla+EGF/Kringle domains as well as the Gla domain alone from the following panel of proteins: hS (high affinity binder), hZ(mid affinity binder), hPT (mid affinity-kringle containing), hFVII (low affinity-utilizes secondary "recep-tor" that is also up-regulated in cancer), and B0178 (hFVII with increased phospholipid affinity). These proteins poten-tially have varying in vivo binding characteristics that may be beneficial to their use as probes (and, if validated and selective, potentially as therapeutics) and that to date have gone unrecognized.

The general approach was to construct recombinant pro-teins and test them for expression. Assays would then be developed to assess binding. Then, expression and purifica-tion methods would be optimized, followed by quality control of gamma-carboxylation.

Figure 2:
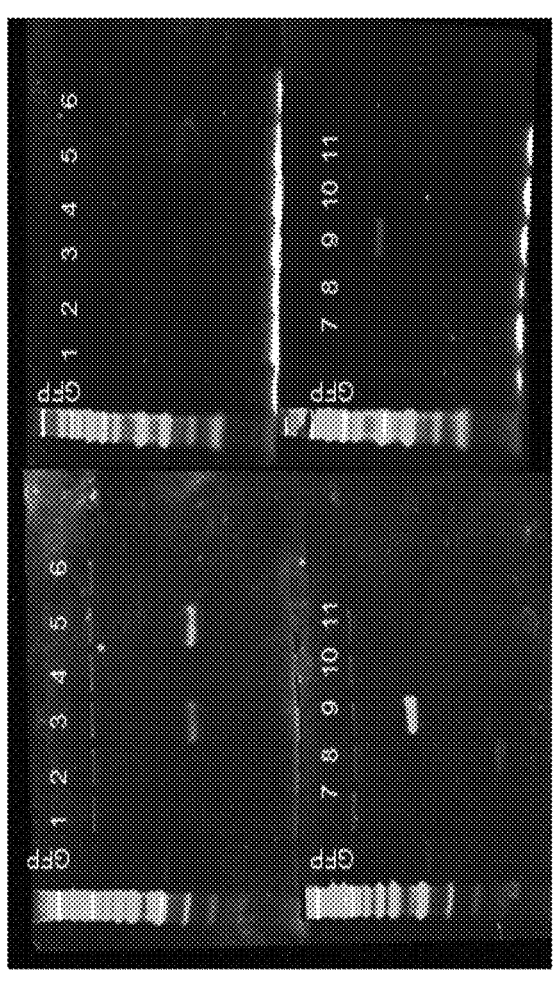
FIG. 2—Testing of Gla domain protein constructs for expression. Transient transfection into 293 cells using 293cellFectin. 10% gels with reduced samples, 23.3 µl of media loaded.
Figure 4:
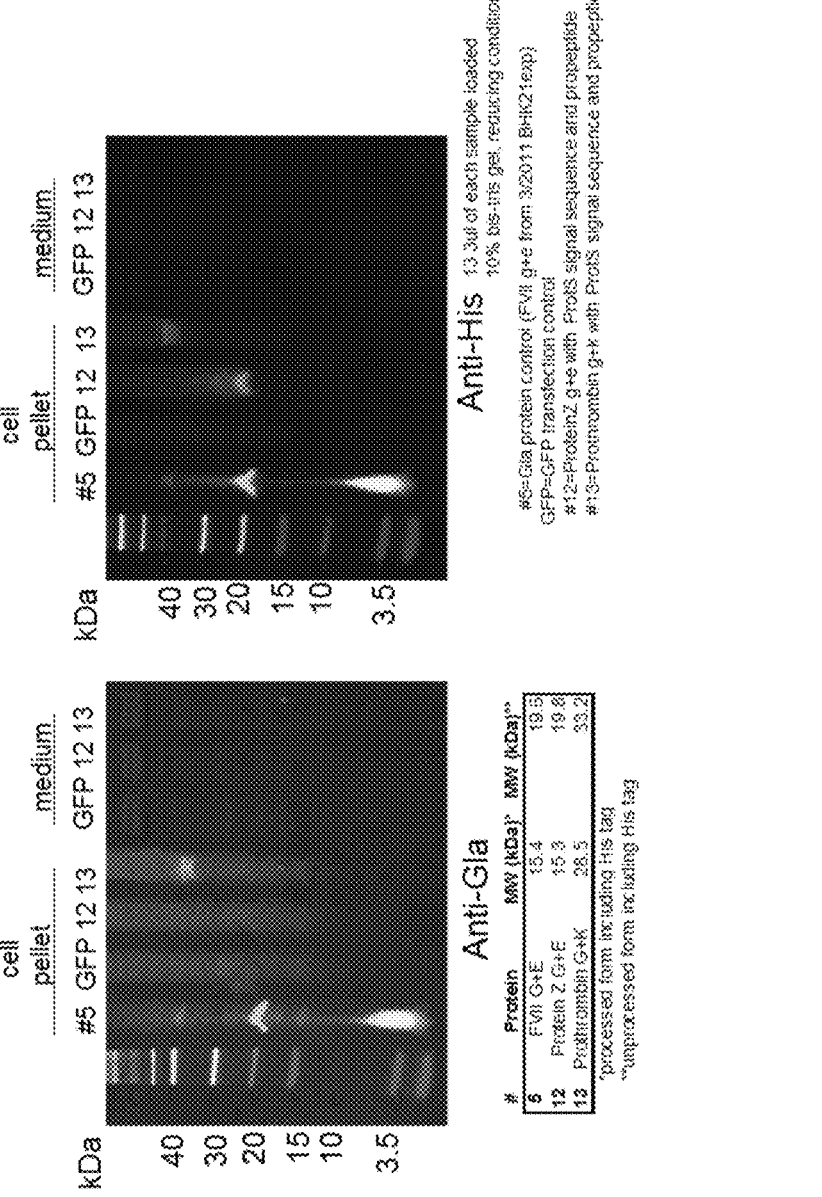
FIG. 4—Changing signal sequence alter secretion. Transient transfection in BHK21 cells. 10% gels with reduced samples, 13.3 µl loaded.

FIG. 1 shows sequences from a variety of Gla domain proteins including carboxylation sites. FIG. 2 shows the expression of a variety of different Gla domain proteins that were engineered and transiently expressed in 293 cells. FIG. 3 shows a similar study in BHK21 cells. Given that one of the best expressing constructs was a Protein S+EGF con-struct, the signal sequence from Protein S was utilized with Prothrombin Gla+Kringle and Protein Z+EGF. However, expression was only observed intracellularly (FIG. 4).

Protein S Gla+EGF was selected for further study. The sequence is shown in FIG. 5. Protein was produced in BHK21 cells using RF286 medium. 600 ml was harvested and concentrated 4×. Purification utilized three steps:

1. Ni-NTA column, 10 ml, fresh packed. The medium are loaded to column and eluted with Imidazole gradient. All the fractions are subject to Gla western blot to identify the His tagged Gla protein S G+E.

2. Hitrap Q with $CaCl_2$ step elution. The Gla positive fractions are pooled and subject to 1 ml Hitrap Q with 10 mM $CaCl_2$ elution.

Figure 6:
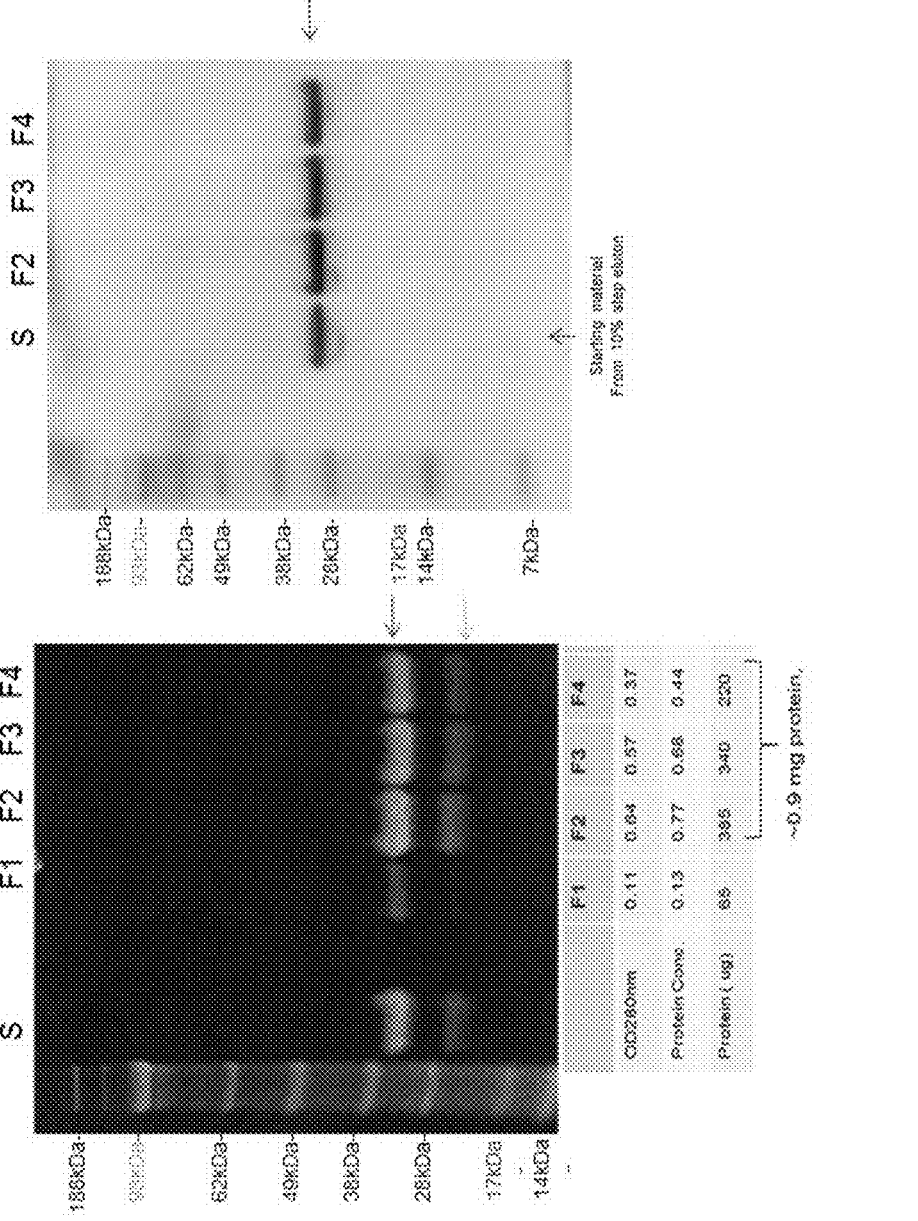
FIG. 6—Purification of Protein S Gla+EGF. F1-F4 are column chromatography fractions. 10% gels, non-reducing conditions.

3. Hitrap Q with $CaCl_2$ gradient (0-10 mM shadow gradient). The step purified Gla proteins were applied to Q and eluted with gradient $CaCl_2$ (up to 10 mM). A total of 0.9 mg of protein at a 95% purity level was produced. FIG. 6 shows the purification fractions under both reducing and non-reducing conditions. FIGS. 7 and 8 show different FACs-based apoptosis assays. Both show that the Protein S Gla+EGF construct is specific for cells undergoing apoptosis just like Annexin V (FIG. 7), and that Annexin V can compete off the Protein S Gla+EGF binding.

In summary, Protein S Gla+EGF was expressed and purified. Analysis on the purified material suggested that it was highly gamma-carboxylated. FACs-based Apoptosis Assays demonstrated that Protein S G+E (11 Gla) could bind to "apoptotic" cells, and that this binding was to cells was via targeting of phosphatidylserine, as demonstrated by Annexin V competition assays.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Patent Appln. 2005/0015232
U.S. Patent Appln. 2004/001827A1
U.S. Patent Appln. 2003/104578A2
U.S. Patent Appln. 2003/104578A1
WO06096515A2
WO07047504A2
WO06096515A2

Aaronson and Horvath, *Science,* 296(5573):1653-5, 2002.
Abe and Kufe, *Cancer Res.,* 49(11):2834-2839, 1989.
Agata et al., *Cancer Res.,* 68:6136-44, 2008.
Ahmad et al., *Cancer Res.,* 68:2920-2926, 2008.
Ahmad et al., *J. Biol. Chem.,* 281:35764-9, 2006.
Ahmad et al., *Nat. Cell Biol.,* 9:1419-1427, 2007.
Alvarez et al., *Cancer Res.,* 65(12):5054-62, 2005.
Alvarez et al., *Cancer Res.,* 66(6):3162-8, 2006.
Anderson et al., *Trends Immunol* 27, 343-348, 2006.
Ashkenazi and Chamow, *Curr Op Immunol* 9, 195-200, 1997.
Baldus et al., *Clin. Cancer Res.,* 10(8):2790-2796, 2004.
Blankenberg, *Proc Am Thorac Soc,* 6, p 469-476, 2009.
Bodanszky et al., *J. Antibiot.,* 29(5):549-53, 1976.
Boersma et al., *J Nuclear Med,* 46 (12), p 2035-2050, 2005.
Bowman et al., *Oncogene,* 19(21):2474-88, 2000.
Bromberg et al., *Cell,* 98(3):295-303, 1999.
Buerger et al., *J. Biol. Chem.,* 278(39):37610-21, 2003.
Carter, *Nature Reviews Immunol* 6, 343-357, 2006.
Chapman, *Advanced Drug Delivery Reviews* 54, 531-545, 2002.
Chaudhury et al., *J Exper Med* 197, 315-322, 2003.
Chen & Greene, *Mol. Cell. Biol.* 5:392-401, 2004.
Cohen et al., *J. Med. Chem.,* 33:883-894, 1990.
Cohen et al., *Cell Res,* 19 p 625-637, 2009.
Duraisamy et al., *Gene,* 373:28-34, 2006.
Duttaroy et al., *Diabetes* 54, 251-258, 2005.
Elliott et al., *Nat Biotechnol* 21, 414-421, 2003.
Elltiot et al., *Nature,* 461, p 2-286, 2009.
Elltiot and Ravichandran, *J. Cell Biol,* 189 (7) p 1059-1070, 2010.
Erwig and Henson, *Cell Death Differentiation* 15, p 243-250, 2008.
Fischer, *Med. Res. Rev.,* 27(6):755-796, 2007.
Gaemers et al., *J. Biol. Chem.,* 276:6191-6199, 2001.
Gendler et al., *J. Biol. Chem.,* 263:12820-12823, 1988.
Germain and Frank, *Clin. Cancer Res.,* 13(19):5665-9, 2007.
Gerondakis et al., *Oncogene* 25(51):6781-99, 2006.
Ghetie et al., *Nature Biotechnol* 15, 637-640, 1997.
Ghosh et al., *Annu. Rev. Cell. Dev. Biol.,* 16:225-60, 1998.
Gilmore, available from NF-kB.org, 2008.
Grillot et al., *J. Immunol.,* 158:4750-7, 1997.
Gronenborn et al., *Anal. Chem.,* 62(1):2-15, 1990.
Hansson and Stenflo. *J Thrombosis Haemostasis,* 3, P 2633-2648, 2005.
Hayden and Ghosh, *Cell,* 132:344-62, 2008.
Hinton et al., *J Immunol* 176, 346-356, 2006.
Hodel et al., *Mol. Cell,* 10(2):347-58, 2002.
Hoffman et al., *Oncogene,* 25:6706-16, 2006.
Huang et al., *Cancer Biol Ther.,* 2:702-706, 2003.
Huang et al., *Cancer Res.,* 65:10413-10422, 2005.
Huxford et al., *Cell* 95(6):759-70, 1998.
Jackson, *Seminars in Oncology,* 24:L164-172, 1997.
Jacobs et al., *Cell,* 95:749-58, 1998.
Jain et al., *Trends Biotechnol* 25, 307-316, 2007.
Johnson et al., *In: Biotechnology And Pharmacy,* Pezzuto et al. (Eds.), Chapman and Hall, NY, 1993.
Jones et al., *J. Med. Chem.,* 39:904-917, 1996.
Karin & Lin, *Nat. Immunol.,* 3:221-7, 2002.
Kau et al., *Nat. Rev. Cancer,* 4(2):106-17, 2004.
Kawano et al., *Cancer Res.,* 67:11576-84, 2007.
Keyt et al., *Proc Natl Acad Sci USA* 91, 3670-3674, 1994.
Kietselaer et al., *Netherlands Heart J,* 10(7/8), p 313-317, (002.
Kinlough et al., *J Biol. Chem.,* 279(51):53071-53077, 2004.
Kufe et al., *Hybridoma,* 3:223-232, 1984.

US 12,678,481 B2

33

Kurihara et al., *Appl Radiat Isot,* 66(9); p 1175-1182, 2008.
Lagow and Carson, *J Cell. Biochem.,* 86:759-72, 2002.
Lahorte et al., Eur *J Nuclear Medicine Mol Imaging,* 31 (6), p 887-919, 2004.
Lee et al., *Cancer Cell,* 15(4):283-293, 2009.
Leng et al., *J Biol. Chem.,* 282:19321-19330, 2007.
Levitan et al., *J. Biol. Chem.,* 280:33374-33386, 2005.
Levy and Shoseyov, *Biotechnol Advances* 20, 191-213, 2002.
Li et al., *Cancer Biol. Ther.,* 2:187-193, 2003b.
Li et al., *J. Biol. Chem.,* 276:35239-35242, 2001.
Li et al., *J Biol. Chem.,* 276:6061-6064, 2001.
Li et al., *Mol. Cancer Res.,* 1:765-775, 2003c.
Li et al., *Mol. Cell Biol.,* 18:7216-7224, 1998.
Li et al., *Oncogene,* 22:6107-6110, 2003a.
Ligtenberg et al., *J. Biol. Chem.,* 267, 6171-6177, 1992.
Lin et al., *Amino Acids, Published online* 17 Mar. 2010.
Loose et al., *Eur J Nucl Med Mot Imaging,* 2007.
Macao, *Nat. Struct. Mol. Biol.,* 13, 71-76, 2006.
McPherson, *J Biol. Chem.,* 251:6300-6306, 1976.
Melder et al., *Cancer Immunol Immunother* 54, 535-5475, 2005.
Merlo et al., *Cancer Res.,* 49, 6966-6971, 1989.
Merrifield, *J Am. Chem. Soc.,* 85:2149-2154, 1963.
Micheau & Tschopp, *Cell,* 114:181-90, 2003.
Mimura et al., *Mol Immunol* 37, 697-706, 2000.
Muthuswamy, *Nat. Cell Biol.,* 3(9):785-92, 2001.
Naresh et al., *Cancer,* 91(3), p 578-548, 2001.
Natoli et al., *Nat. Immunol.,* 6:439-45, 2005.
Navia et al., *Curr. Opin. Struct. Biol.,* 2:202-210, 1992.
Nelsestuen, *Trends Cardiovasc Med,* 9(6), p 162-167, 1999.
Osborn et al., *J Pharmacol Experimental Therapeutics* 303, 540-548, 2002a.
Osborn et al., Eur J Pharmacol 456, 149-158, 2002b.
Pasparakis et al., *Cell Death Differ.* 13:861-72, 2006.
PCT Appln. PCT/US00/03745
PCT Appln.PCT/US00/14667
PCT Appln.PCT/US99/11913
PCT Appln.PCT/US99/18441
Peptide Synthesis, 1985
Percipalle et al., *J. Mol. Biol.,* (4):722-32, 1997.
Perey et al., *Cancer Res.,* 52(22):6365-6370, 1992.
Petkova et al., *International Immunol* 18, 1759-1769, 2006a.
Protective Groups in Organic Chemistry, 1973
Protein NMR Spectroscopy, Principles and Practice, J. Cavanagh et al., Academic Press, San Diego, 1996.
Raina et al., *Direct targeting of the GLA DOMAIN oncoprotein blocks survival and tumorigenicity of human breast carcinoma cells. Cancer Res.,* 2009 (IN PRESS).
Raina et al., *EMBO J.,* 25:3774-3783, 2006.
Raina et al., *J. Biol. Chem.,* 279:20607-20612, 2004.
Raju and Scallon, *Biotechnol Prog* 23, 964-971, 2007.
Raju, and Scallon, *Biochem Biophys Res Commun* 341, 797-803, 2006.
Ramasamy et al., *Mol. Cell,* 27:992-1004, 2007.

34

Remington's Pharmaceutical Sciences, 15th Ed., 1035-1038 and 1570-1580, 1990.
Remington's Pharmaceutical Sciences, 15th Ed., 3:624-652, 1990.
Ren et al., *Cancer Cell,* 5:163-175, 2004.
Ren et al., *J. Biol. Chem.,* 277:17616-17622, 2002.
Reutelingsperger et al., *J Immunol Methods* 265, 123-132, 2002.
Ryan and Wente, *Curr. Opin. Cell Biol.,* 12(3):361-71, 2000.
Schneider-Brachert et al., *Immunity,* 21:415-28, 2004.
Schroeder et al., *J. Biol. Chem.,* 276(16):13057-13064 2001.
Schroeder et al., *Oncogene,* 23:5739-5747, 2004.
Shah et al., *Proc. Natl. Acad. Sci. USA* 95, p 4229-4234, 1998.
Shuai, *Oncogene,* 19(21):2638-44, 2000.
Siddiquee et al., *Proc. Natl. Acad. Sci. USA,* 104(18):7391-6, 2007.
Siddiqui et al., *Proc. Natl. Acad. Sci. USA,* 85:2320-2323, 1988.
Sinclair and Elliott, *J Pharmaceutical Sci* 94, 1626-1635, 2005.
Solid Phase Peptide Synthelia, 1984
Song et al., *Proc. Natl. Acad. Sci. USA,* 102(13):4700-5, 2005.
Soule et al., *Cancer Res.,* 50(18):6075-6086, 1990.
Suh and Gumbiner, *Exp. Cell Res.,* 290(2):447-56, 2003.
Sung et al., *J Interferon Cytokine Res* 23, 25-36, 2003.
Tait and Gibson. *Arch Biochem Biophys.* 298(1), p 187-191, 1992.
Truscott et al., *J Cell Biol.,* 163(4):707-713, 2003.
Umana et al., *Nat Biotechnol* 17, 176-180, 1999.
Vaccaro et al., *Nature Biotechnol* 23, 1283-1288, 2005.
van den Eijnde et al., *J Cell Science,* 114, p 3631-3642, 2001.
Vermeer et al., *Nature,* 422(6929):322-6, 2003.
Veronese and Pasut, *Drug Discovery Today* 10, 1451-1458, 2005.
Webb et al., *J Immunol,* 169 p 2580-2586, 2002.
Weber, *Advances Protein Chem.,* 41:1-36, 1991.
Wegenka et al., *Mol. Cell Biol.,* 14(5):3186-96, 1994.
Wei et al., *Cancer Cell,* 7:167-178, 2005.
Wei et al., *Cancer Res.,* 67(4):1853-8, 2007.
Wei et al., *Mol. Cell.,* 21:295-305, 2006.
Weis, *Cell,* 112(4):441-51, 2003.
Wen et al., *J. Biol. Chem.,* 278:38029-38039, 2003.
Wider, *BioTechniques,* 29:1278-1294, 2000.
Yamamoto et al., *J. Biol. Chem.,* 272:12492-12494, 1997.
Yeh et al., Proc. *Nat'l Acad. Sci. USA* 89, 1904-1908, 1992.
Yin et al., *J. Biol. Chem.,* 278:35458-35464, 2003.
Yin et al., *J. Biol. Chem.,* 279:45721-45727, 2004.
Yin et al., *J. Biol. Chem.,* 282:257-266, 2007.
Young et al., *Cell.* 112(1):41-50, 2003.
Yu et al., *Seminars Thrombosis Hemostasis,* 30(1), p 21-30, 2004.
Yu and Jove, *Nat. Rev. Cancer,* 4(2):97-105, 2004.
Zhang et al., *Mol. Cell. Biol.,* 19:7138-7146, 1999.

The invention claimed is:

1. A diagnostic probe molecule for detection of apoptosis by targeting phosphatidylserine cell-surface expression in vivo, said probe molecule comprising:

a polypeptide comprising a protein S gamma-carboxyglu-tamic-acid (Gla) domain and a protein S Epidermal Growth Factor (EGF) domain, and wherein the poly-peptide is fused to a proteinaceous sequence compris-ing a detectable label or a proteinaceous sequence conjugated to a detectable label;

wherein said probe molecule does not contain a serine protease domain from a Gla domain protein and also does not contain a hormone-binding domain from a Gla domain protein; and wherein said polypeptide comprises SEQ ID NO: 6 or a derivative differing therefrom only in the absence of the His-tag.

2. The diagnostic probe molecule according to claim 1, wherein the polypeptide is 300 amino acids or less.

3. The diagnostic probe molecule according to claim 1, wherein the polypeptide comprises SEQ ID NO:6.

4. The diagnostic probe molecule according to claim 1, wherein the fused proteinaceous sequence comprises an Fc region.

5. The diagnostic probe molecule according to claim 1, wherein the detectable label is selected from the group consisting of a fluorescent label, a chemiluminescent label, a radiolabel, an enzyme, a dye, a ligand, a hapten, a phosphorescent molecule, a chromophore, a photoaffinity molecule, a colored particle, a NMR-detectable substance, and an X-ray imaging agent.

6. The diagnostic probe molecule according to claim 1, wherein the label is conjugated to said fused proteinaceous sequence.

7. A pharmaceutical composition comprising the diagnos-tic probe molecule of claim 1 and a pharmaceutically acceptable carrier or aqueous medium.

8. The diagnostic probe molecule according to claim 1 wherein the label is a paramagnetic ion selected from chromium (III), manganese (II), iron (III), iron (II), cobalt (II), nickel (II), copper (II), neodymium (III), samarium (III), ytterbium (III), gadolinium (III), vanadium (II), ter-bium (III), dysprosium (III), holmium (III) erbium (III), and combinations thereof.

9. The diagnostic probe molecule according to claim 1 wherein the label is a radioactive isotope selected from astatine$^{211}$, $^{14}$carbon, $^{51}$chromium, $^{36}$chlorine, $^{57}$coba-lt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phos-phorus, rhenium$^{186}$, rhenium$^{188}$, $^{75}$selenium, $^{35}$sulphur, technicium$^{99m}$, yttrium$^{90}$ and combinations thereof.

10. The diagnostic probe molecule according to claim 1, wherein the label is fluorescent and selected from 7-amino-4-methylcoumarin-3-acetic acid, boron-dipyrromethene 630/650, boron-dipyrromethene 650/665, boron-dipyr-romethene fluorescein analog, boron-dipyrromethene rhod-amine 6G analog, boron-dipyrromethene tetramethylrhod-amine analog, Cyanine 3, Cyanine 5, 6-Carboxyfluorescein, Fluorescein Isothiocyanate, Hexachloro-fluorescein, 6-Car-boxy-4',5'-dichloro-2',7'-dimethoxyfluorescein, 2',7'-difluo-rofluorescein 488, 2',7'-difluorofluorescein 500, 2',7'-difluo-rofluorescein 514, 7-Amino-4-methylcoumarin, Carboxy-X-rhodamine, Tetrachloro-fluorescein, Tetramethylrhodamine and Sulforhodamine 101 acid chloride.

* * * * *